United States Patent [19]
Adachi et al.

[11] Patent Number: 4,873,334
[45] Date of Patent: Oct. 10, 1989

[54] 4,7-DIHYDROPYRAZOLO(3,4-B) PYRIDINE DERIVATIVES

[75] Inventors: Ikuo Adachi, Osaka; Teruo Yamamori, Hyogo; Motohiko Ueda, Osaka; Hatsuo Sato, Nara, all of Japan

[73] Assignee: Shionogi & Co., Ltd., Osaka, Japan

[21] Appl. No.: 99,907

[22] Filed: Sep. 22, 1987

Related U.S. Application Data

[63] Continuation-in-part of Ser. No. 709,795, Mar. 8, 1985, abandoned, which is a continuation-in-part of Ser. No. 18,815, Feb. 19, 1987, abandoned, which is a continuation of Ser. No. 527,733, Aug. 30, 1983, abandoned.

[30] Foreign Application Priority Data

Oct. 5, 1982 [JP] Japan ................................. 57-176763
Mar. 19, 1984 [JP] Japan ................................. 69-53118

[51] Int. Cl.$^4$ ..................... A61K 31/44; C07D 471/04
[52] U.S. Cl. ..................................... 514/303; 546/120
[58] Field of Search ......................... 546/120; 514/303

[56] References Cited

U.S. PATENT DOCUMENTS 4,562,256 12/1985 Adachi et al. ...................... 546/120

FOREIGN PATENT DOCUMENTS 0107619 5/1984 European Pat. Off. .
0114273 8/1984 European Pat. Off. .

Primary Examiner—Mary C. Lee
Assistant Examiner—Bernard I. Dentz
Attorney, Agent, or Firm—Wenderoth, Lind & Ponack

[57] ABSTRACT

Novel Ca-blockers, 4,7-dihydropyrazolo[3,4-b]pyridine derivatives having potent antihypertensive and coronary vasodilating actions and useful in treatment for diseases in circulatory system, but without systole inhibitory action.

18 Claims, No Drawings

4,7-DIHYDROPYRAZOLO(3,4-B) PYRIDINE DERIVATIVES

This is a CIP application of U.S. application Ser. No. 709,795 filed Mar. 8, 1985 now abandoned, and U.S. application Ser. No. 018,815, filed Feb. 19, 1987 now abandoned, the latter application being a continuation of U.S. application Ser. No. 527,733, filed Aug. 30, 1983 now abandoned.

BACKGROUND OF THE INVENTION

(1) Field of the Invention

The compounds this invention provides are novel Cablocker-type cardiovascular agents having potent antihypertensive and coronary vasodilating effects, and useful in treatment for cardiovascular diseases such as angina pectoris, hypertension, cerebrovascular dysfunction, arrhythmia or the like.

(2) Prior Art

Compounds having Ca-blocking effect have commonly been used for treatment of cardiovascular diseases such as angina pectoris, hypertention, cerebrovascular dysfunction, arrhythmia or the like, and have become well-known because of their high efficacy. In particular, a series of 1,4-dihydropyridine derivatives have been investigated extensively and developed as Ca-blocker. Examples of useful Ca-blockers are Nifedipine (U.S. Pat. Nos. 3,485,847 and 3,644,627), Nisoldipine (Japanese Patent Publication No. 56-47185), 2-amino-1,4-dihydropyridine derivatives (JPN Pat. Pub. No. 57-20306), Nicardipine (JPN Unexamined Pat. Pub. No. 49-109384), 2-pyridyl-1,4-dihydropyridine derivatives (JPN Unexam. Pat. Pub. No. 54-48796), 2-methyl-dihydropyridine derivatives (JPN Unexam. Pat. Pub. No. 55-62065) and the like. Some examples of pyrazolodihydropyridine derivatives, the production thereof and their Ca-blocking action are disclosed in JPN Pat. Application Nos. 57-176763 and 58-166258 by the present inventors.

SUMMARY

The present invention relates to novel 4,7-dihydropyrazolo[3,4-b]pyridine derivatives and agents for treating cardiovascular diseases. More particularly it relates to 4,7-dihydropyrazolo[3,4-b]pyridine derivatives represented by the formula:

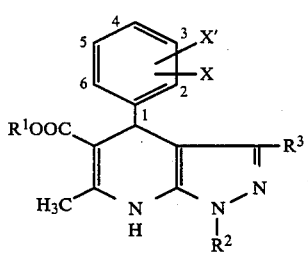

(I)

wherein X and X' each is hydrogen, nitro, or halogen which may be located at the position or positions 2, 3, and/or 6; $R^1$ is (a) straight or branched chain $C_1$-$C_8$ alkyl, (b) $C_4$-$C_6$ cycloalkyl which may be substituted by lower alkyl, (c) $C_3$-$C_7$ cycloalkyl($C_1$-$C_4$)alkyl, (d) $C_1$-$C_4$ alkoxy($C_1$-$C_4$)alkyl, (e) $C_4$-$C_7$ cycloalkyloxy($C_1$-$C_4$)alkyl, (f) phenoxy($C_1$-$C_4$)alkyl, (g) $C_1$-$C_4$ alkylthio($C_1$-$C_4$)alkyl, (h) $C_4$-$C_7$ cycloalkylthio($C_1$-$C_4$)alkyl, (i) phenylthio($C_1$-$C_4$)alkyl, (j) $C_1$-$C_4$ monoalkylamino or $C_2$-$C_8$ dialkylamino-substituted ($C_1$-$C_4$)alkyl, (k) tetrahydrofuryl($C_1$-$C_4$)alkyl, (l) phenyl($C_1$-$C_3$)alkyl, which may have one or more substituents of halogen, $C_1$-$C_4$ alkoxy, or trifluoroalkyl, (m) N-benzylpyrrolidinyl, or (n) N-benzylpiperidinyl; $R^2$ is hydrogen, $C_1$-$C_4$ alkyl, $C_4$-$C_6$ cycloalkyl, or phenyl; and $R^3$ is hydrogen, $C_1$-$C_8$ straight or branched chain alkyl, $C_3$-$C_7$ cycloalkyl which may be substituted by $C_1$-$C_4$ alkyl, phenyl which may be substituted by chlorine, trifloromethyl, cyano, methoxy, methoxycarbonyl or ethoxycarbonyl, $C_7$-$C_9$ aralkyl, $C_1$-$C_4$ alkoxycarbonyl or 5-or 6-membered heterocyclic group consisting of a α-pyridyl, β-furyl and 1-methylimidazol-2-yl; or pharmaceutically acceptable acid addition salts thereof.

The objective compounds (I) of this invention are prepared through the Michael addition between heterocyclic amines and α, β-unsaturated ketones accompanied by cyclization reaction. More particularly, the compounds (I) can be produced by the process comprising reacting a compound represented by the formula:

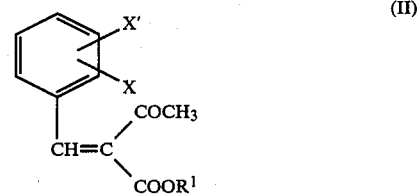

(II)

wherein $R^1$ has the same meaning as defined above, with a compound represented by the formula:

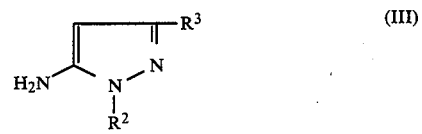

(III)

wherein $R^2$ and $R^3$ each has the same meaning as defined above.

Incidentally, the compounds of this invention have the advantage that they have no systole inhibitory action as an adverse reaction usually seen in the use of the analogous known compounds.

DESCRIPTION OF THE PREFERRED ENBODIMENT

In the definition in the formulae (I) to (III), halogen means fluorine, chlorine, bromine, and iodine and, particularly, chlorine is preferred.

Straight or branched chain $C_1$-$C_8$ alkyl includes, for example, methyl, ethyl, i-propyl, t-butyl, n-pentyl, iso-pentyl, sec-pentyl, neo-pentyl, tert-pentyl, 3-methyl-pent-3-yl, n-hexyl, iso-hexyl, sec-hexyl, neo-hexyl, tert-hexyl, n-heptyl, iso-heptyl, sec-heptyl, neo-heptyl, tert-heptyl, n-octyl, iso-octyl, sec-octyl, and the like.

$C_4$-$C_6$ Cycloalkyl which may be substituted by lower alkyl includes, for example, cyclobutyl, cyclopentyl, cyclohexyl, 2-i-propyl-4-methylcyclohexyl and the like.

$C_3$-$C_7$ Cycloalkyl includes cyclopropyl, cyclobutyl, cyclohexyl, cycloheptyl and the like.

$C_1$-$C_4$ Alkoxy includes methoxy, ethoxy, n-propoxy, isopropoxy, n-butoxy, iso-butoxy, tert-butoxy and the like.

$C_4$-$C_7$ cycloalkyloxy includes cyclobutyloxy, cyclopentyloxy, cyclohexyloxy and the like.

$C_1-C_4$ Alkylthio includes methylthio, ethylthio, n-propylthio, iso-propylthio, n-butylthio, iso-butylthio, secbutylthio, tert-butylthio and the like.

$C_4-C_7$ Cycloalkylthio includes cyclobutylthio, cyclopentylthio, cyclohexylthio, cycloheptylthio and the like.

$C_1-C_4$ Monoalkylamino includes methylamino, ethylamino, n-propylamino, iso-propylamino, n-butylamino, iso-butylamino, sec-butylamino, tert-butylamino and the like and $C_2-C_8$ dialkylamino includes dimethylamino, methylethylamino, methyl(n-propyl)amino, methyl(iso-propyl)amino, diethylamino, methyl(n-butyl)amino, methyl(iso-butyl)amino, methyl(secbutyl)amino, methyl(tert-butyl)amino, ethyl(n-propyl)amino, ethyl(iso-propyl)amino, ethyl(n-butyl)amino, ethyl(iso-butyl)amino, ethyl(sec-butyl)amino, ethyl(tert-butyl)amino, dipropylamino, n-propyl(n-butyl)amino, n-propyl(iso-butyl)amino, n-propyl(sec-butyl)amino, n-propyl(tert-butyl)amino, iso-propyl(n-butyl)amino, iso-propyl(iso-butyl)amino, isopropyl(sec-butyl)amino, iso-propyl(tert-butyl)amino, dibutylamino and the like.

Tetrahydrofuryl($C_1-C_4$)alkyl includes, for example, 2-tetrahydrofurylmethyl, 3-tetrahydrofurylethyl, and the like.

Phenyl($C_1-C_3$)alkyl which may have one or more substituents of halogen, ($C_1-C_4$)alkoxy, or trifluoroalkyl includes, for example, benzyl, phenetyl, 3-phenylpropyl, tolylmethyl, 4-fluorophenethyl, 4-chlorophenethyl, 4-bromophenethyl, 4-iodophenethyl, 3,4-dimethoxyphenethyl, 1-methoxy-2-phenethyl and the like.

Particularly, $-NO_2$ is the most preferable substituent for X in formulae (I) and (II) and is preferably substituted at the 2 or 3 position of the phenyl.

A preferred group of compounds according to the present invention are 4,7-dihydropyrazolo[3,4-b]pyridine derivatives represented by the formula:

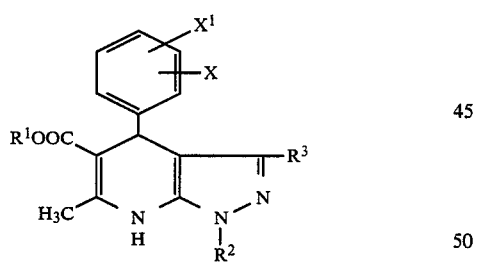

wherein X and $X^1$ each is hydrogen, nitro, or halogen which may be located at the position or positions 2, 3, and/or 6;

$R^1$ is $C_1-C_4$ alkyl; $R^2$ is hydrogen, $C_1-C_4$ alkyl, $C_4-C_6$ cycloalkyl, or phenyl;

$R^3$ is hydrogen, $C_1-C_8$ straight or branched chain alkyl, $C_3-C_7$ cycloalkyl which may be substituted by $C_1-C_3$ alkyl, phenyl which may be substituted by chlorine, trifluoromethyl, cyano, methoxy, methoxycarbonyl or ethoxycarbonyl, $C_7-C_9$ aralkyl or $C_1-C_4$ alkoxycarbonyl; or pharmaceutically acceptable acid addition salts thereof.

Also, a particularly preferred group of compounds according to the present invention are 4,7-dihydropyrazolo[3,4-b]-pyridine derivatives represented by the formula:

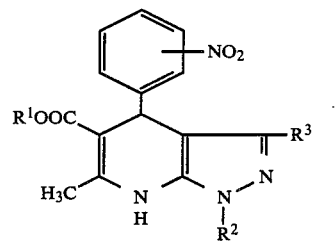

wherein $R^1$ is (a) straight or branched chain $C_5-C_8$ alkyl, (b) $C_4-C_6$ cycloalkyl which may be substituted by lower alkyl, (c) $C_3-C_7$ cycloalkyl ($C_1-C_4$)alkyl, (d) $C_1-C_4$ alkoxy-($C_1-C_4$)alkyl, (e) $C_4-C_7$ cycloalkyloxy($C_1-C_4$)alkyl, (f) phenoxy($C_1-C_4$)alkyl, (g) $C_1-C_4$ alkylthio($C_1-C_4$)alkyl, (h) $C_4-C_7$ cycloalkylthio($C_1-C_4$)alkyl, (i) phenylthio($C_1-C_4$)alkyl, (j) $C_1-C_4$ monalkylamino or $C_2-C_8$ dialkylamino-substituted ($C_1-C_4$)alkyl, (k) tetrahydrofuryl($C_1-C_4$)alkyl, (l) phenyl($C_1-C_3$)alkyl, which may have one or more substituents of halogen or $C_1-C_4$ alkoxy, (m) N-benzylpyrrolidinyl, or (n) N-benzylpiperidinyl; $R^2$ is $C_1-C_4$ alkyl; and $R^3$ is $C_4-C_6$ cycloalkyl or $C_3-C_7$ cycloalkyl-($C_1-C_4$)alkyl; and the pharmaceutically acceptable acid addition salts thereof.

The invention also contemplates agents for treating cardiovascular diseases containing at least one of said compounds described above and a pharmaceutically acceptable carrier.

The compound (I) of the present invention can, as shown in the following scheme, be readily produced by the reaction of α,β-unsaturated ketone reagent (II) with a 5-aminopyrazole (III),

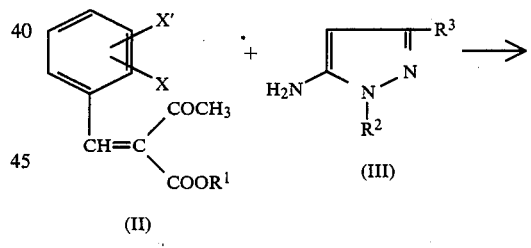

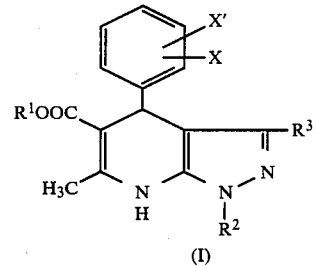

wherein X, X', $R^1$, $R^2$ and $R^3$ each has the same meaning as identified above.

The reaction may be accomplished in the absence or presence of any solvent. Such a solvent as employed for this reaction includes alcohols such as methanol, ethanol, isopropanol, tert-butanol, ethylene glycol and the like; hydrocarbons such as benzene, toluene, xylene and the like; ethers such as ether, tetrahydrofuran, dioxane, glyme, diglyme and the like; halogenohydrocarbons such as dichloromethane, chloroform, dichloroethane, carbon tetrachloride and the like; esters such as ethyl acetate; acetic acid; dimethylformaminde; pyridine; and the like. An acid, an organic base or the like is employed as a catalyst, if necessary. Such an acid includes inorganic acids e.g., sulfuric acid, hydrochloric acid, phosphoric acid and the like; para-toluenesulfonic acid, acetic acid, formic acid and the like as an organic acid; and boron trifluoride, zinc chloride, alminium chloride, magnesium chloride, tin chloride and the like as a Lewis acid. Such a base includes organic base catalysts e.g., triethylamine, pyridine, pyrrolidine, piperidine and the like.

The reaction is completed after a few hours or a few days at room temperature (1°–30° C.) or under heating (30°–100° C.).

The starting compounds, 5-aminopyrazole and α,β-unsaturated ketone reagents, both of which are employed in the reaction, may be prepared in the manners as shown below, respectively.

(i) Preparation of 5-aminopyrazole (III);

A 5-aminopyrazole (III) can be produced according to the reaction sequence as shown below. In other words, it can be prepared in a high yield by the cyclization of a hydrazine (VI) with a β-ketonitrile (VII).

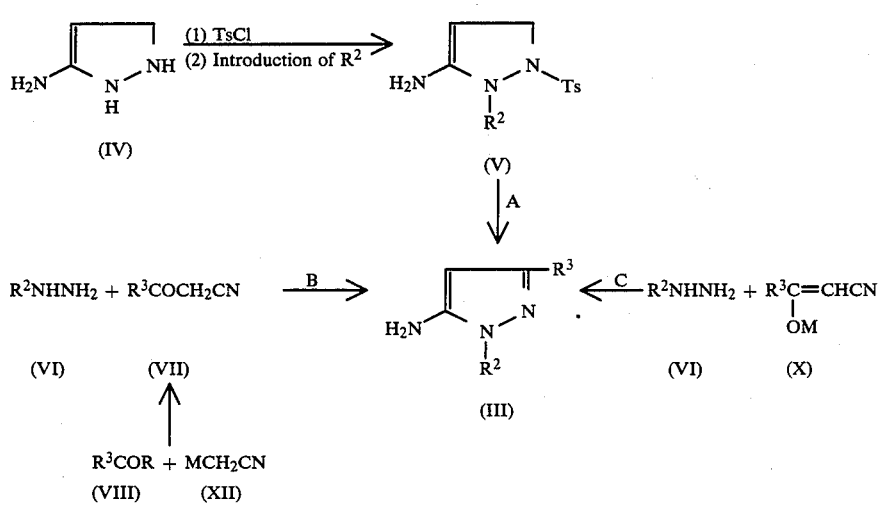

wherein $R^2$ and $R^3$ each has the same meaning as defined above, R represents halogen or an ester residue, and M represents an alkali metal.

In the above reaction sequence, the 5-aminopyrazole compounds (III) wherein $R^3$ is hydrogen may be prepared according to the process A from the compounds (IV) by tosylation and introduction of $R^2$ followed by elimination of the tosyl group with a base [Chem. Ber. 98, 3368 (1965)]. The compounds (III) wherein $R^3$ is neither hydrogen nor alkoxycarbonyl may be prepared according to the process B by cyclization reaction of hydrazine or methyl- or phenyl-hydrazines (VI) with a member of β-ketonitriles (VII). The β-ketonitriles (VI) are prepared by reaction of a member of acid chrolides (VIII) with an alkali metal salt of acetonitrile (XII). The compounds (III) wherein $R^3$ is alkoxycarbonyl are prepared by cyclization reaction of a member of hydrazines (VI) with the alkali metal salt of alkyl 3-cyanopyruvates (X).

(ii) Preparation of α,β-unsaturated ketone reagents (II):

α,β-Unsaturated ketone reagents (II) are prepared, as shown in the following scheme, by the condensation reaction of an aldehyde (XI) with an acetoacetic ester (IX); the manner of the reaction is disclosed in J. Chem. Soc., 81, 1212(1902); Chem. Ber., 29, 172(1896); Ann., 218, 170 (1883); J. Chem. Soc., 3092 (1962).

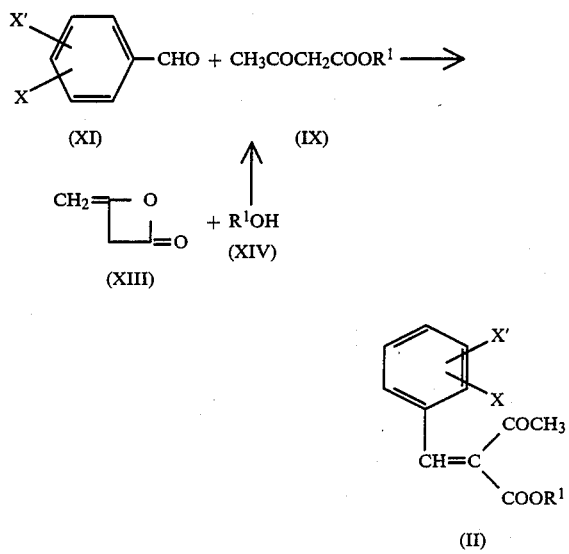

wherein X, X', and $R^1$ each has the same meaning as defined above.

The acetoacetic esters are prepared, in the presence of an acid-(hydrochloric acid, sulfuric acid, phospholic acid and the like) or base-(pyridine, pyrrolidine, piperidine and the like) catalyst, through the reaction of a diketene (XIII) with an alcohol (XIV).

The typical compounds of the present invention, which are prepared by the reaction of the above-obtained α,β-unsaturated ketone reagents (II) with a 5-aminopyrazole (III), are as follows.

(Compounds list part 1)

Ethyl 3-cyclopentyl-1,6-dimethyl-4-(3-nitrophenyl)-4,7-dihydropyrazolo[3,4-b]pyridine-5-carboxylate, Ethyl 1,6-dimethyl-4-(3-nitrophenyl)-4,7-dihydropyrazolo[3,4-b]pyridine-5-carboxylate, Methyl 1,6-dimethyl-4-(2-nitrophenyl)-4,7-dihydropyrazolo[3,4-b]pyridine-5-carboxylate,
Methyl 3-isopropyl-1,6-dimethyl-4-(3-nitrophenyl)-4,7-dihydropyrazolo[3,4-b]pyridine-5-carboxylate,
Methyl 3-(n-butyl)-1,6-dimethyl-4-(3-nitrophenyl)-4,7-dihydropyrazolo[3,4-b]pyridine-5-carboxylate,
Methyl 3-cyclobutyl-1,6-dimethyl-4-(3-nitrophenyl)-4,7-dihydropyrazolo[3,4-b]pyridine-5carboxylate,
Methyl 3-cyclopentyl-1,6-dimethyl-4-(2-nitrophenyl)-4,7-dihydropyrazolo[3,4-b]pyridine-5-carboxylate,
Methyl 3-cyclopentyl-1,6-dimethyl-4-(3-nitrophenyl)-4,7-dihydropyrazolo[3,4-b]pyridine-5-carboxylate,
Isopropyl 3-cyclopentyl-1,6-dimethyl-4-(3-nitrophenyl)-4,7-dihydropyrazolo[3,4-b]pyridine-5-carboxylate,
Ethyl 3-cyclopentyl-1,6-dimethyl-4-(2-chlorophenyl)-4,7-dihydropyrazolo[3,4-b]pyridine-5-carboxylate,
Ethyl 3-cyclopentyl-1,6-dimethyl-4-(2,6-dichlorophenyl)-4,7-dihydropyrazolo[3,4-b]pyridine-5-carboxylate,
Methyl 3-cyclohexyl-1,6-dimethyl-4-(3-nitrophenyl)-4,7-dihydropyrazolo[3,4-b]pyridine-5-carboxylate,
Methyl 3-benzyl-1,6-dimethyl-4-(3-nitrophenyl)-4,7-dihydropyrazolo[3,4-b]pyridine-5-carboxylate,
Ethyl 3-phenyl-6-methyl-4-(3-nitrophenyl)-4,7-dihydropyrazolo[3,4-b]pyridine-5-carboxylate,
Ethyl 1,3-diphenyl-6-methyl-4-(3-nitrophenyl)-4,7-dihydropyrazolo[3,4-b]pyridine-5-carboxylate,
Methyl 3-phenyl-1,6-dimethyl-4-(3-nitrophenyl)-4,7-dihydropyrazolo[3,4-b]pyridine-5-carboxylate,
Ethyl 3-phenyl-1,6-dimethyl-4-(3-nitrophenyl)-4,7-dihydropyrazolo[3,4-b]pyridine-5-carboxylate,
Methyl 3-phenyl-1,6-dimethyl-4-(2-nitrophenyl)-4,7-dihydropyrazolo[3,4-b]pyridine-5-carboxylate,
Ethyl 3-(3-chlorophenyl)-1,6-dimethyl-4-(3-nitrophenyl)-4,7-dihydropyrazolo[3,4-b]pyridine-5-carboxylate,
Methyl 3-(3,5-dichlorophenyl)-1,6-dimethyl-4-(3-nitrophenyl)-4,7-dihydropyrazolo[3,4-b]pyridine-5-carboxylate,
Ethyl 3-(3,5-dichlorophenyl)-1,6-dimethyl-4-(3-nitrophenyl)-4,7-dihydropyrazolo[3,4-b]pyridine-5-carboxylate,
Ethyl 3-(3-trifluoromethylphenyl)-1,6-dimethyl-4-(3-nitrophenyl)-4,7-dihydropyrazolo[3,4-b]pyridine-5-carboxylate,
Ethyl 3-(3-cyanophenyl)-1,6-dimethyl-4-(3-nitrophenyl)-4,7-dihydropyrazolo[3,4-b]pyridine-5-carboxylate,
Ethyl 3-(3-methoxycarbonylphenyl)-1,6-dimethyl-4-(3-nitrophenyl)-4,7-dihydropyrazolo[3,4-b]pyridine-5-carboxylate,
Ethyl 3-(3-ethoxycarbonylphenyl)-1,6-dimethyl-4-(3-nitrophenyl)-4,7-dihydropyrazolo[3,4-b]pyridine-5-carboxylate,
Ethyl 3-(α-pyridyl)-1,6-dimethyl-4-(3-nitrophenyl)-4,7-dihydropyrazolo[3,4-b]pyridine-5-carboxylate,
Ethyl 3-(β-furyl)-1,6-dimethyl-4-(3-nitrophenyl)-4,7-dihydropyrazolo[3,4-b]pyridine-5-carboxylate,
Methyl 3-methoxycarbonyl-1,6-dimethyl-4-(3-nitrophenyl)-4,7-dihydropyrazolo[3,4-b]pyridine-5-carboxylate,
Ethyl 3-ethoxycarbonyl-1,6-dimethyl-4-(3-nitrophenyl)-4,7-dihydropyrazolo[3,4-b]pyridine-5-carboxylate,
Methyl 3-isopropoxycarbonyl-1,6-dimethyl-4-(3-nitrophenyl)-4,7-dihydropyrazolo[3,4-b]pyridine-5-carboxylate,
Ethyl 3-(4-methoxyphenyl)-1,6-dimethyl-4-(3-nitrophenyl)-4,7-dihydropyrazolo[3,4-b]pyridine-5-carboxylate,
Methyl 1,3-dicyclopentyl-6-methyl-4-(3-nitrophenyl)-4,7-dihydropyrazolo[3,4-b]pyridine-5-carboxylate,
Methyl 3-isobutyl-1,6-dimethyl-4-(3-nitrophenyl)-4,7-dihydropyrazolo[3,4-b]pyridine-5-carboxylate,
Methyl 3-(t-butyl)-1,6-dimethyl-4-(3-nitrophenyl)-4,7-dihydropyrazolo[3,4-b]pyridine-5-carboxylate,
Methyl 3-(n-pentyl)-1,6-dimethyl-4-(3-nitrophenyl)-4,7-dihydropyrazolo[3,4-b]pyridine-5-carboxylate,
Methyl 3-(3-methylpent-3-yl)-1,6-dimethyl-4-(3-nitrophenyl)-4,7-dihydropyrazolo[3,4-b]pyridine-5-carboxylate,
Methyl 3-cyclopropyl-1,6-dimethyl-4-(3-nitrophenyl)-4,7-dihydropyrazolo[3,4-b]pyridine-5-carboxylate,
Methyl 3-cyclohexyl-1,6-dimethyl-4-(2-nitrophenyl)-4,7-dihydropyrazolo[3,4-b]pyridine-5-carboxylate,
Methyl 3-cycloheptyl-1,6-dimethyl-4-(3-nitrophenyl)-4,7-dihydropyrazolo[3,4-b]pyridine-5-carboxylate,
Methyl 3-(4-methylcyclohexyl)-1,6-dimethyl-4-(3-nitrophenyl)-4,7-dihydropyrazolo[3,4-b]pyridine-5-carboxylate,
Methyl 3-(1-ethylcyclohexyl)-1,6-dimethyl-4-(3-nitrophenyl)-4,7-dihydropyrazolo[3,4-b]pyridine-5-carboxylate,
Methyl 3-(1-methylimidazol-2-yl)-1,6-dimethyl-4-(3-nitrophenyl)-4,7-dihydropyrazolo[3,4-b]pyridine-5-carboxylate, (Compounds list part 2)
(1) 2-Methoxyethyl 3-cyclopentyl-1,6-dimethyl-4-(2-nitrophenyl)-4,7-dihydropyrazolo[3,4-b]pyridine-5-carboxylate,
(2) 2-Methoxyethyl 3-cyclopentyl-1,6-dimethyl-4-(3-nitrophenyl)-4,7-dihydropyrazolo[3,4-b]pyridine-5-carboxylate,
(3) 2-Methoxyethyl 3-cyclohexyl-1,6-dimethyl-4-(2-nitrophenyl)-4,7-dihydropyrazolo[3,4-b]pyridine-5-carboxylate,
(4) 2-Methoxyethyl 3-cyclopentylmethyl-1,6-dimethyl-4-(2-nitrophenyl)-4,7-dihydropyrazolo[3,4-b]pyridine-5-carboxylate,
(5) 2-Isopropoxypropyl 3-cyclopentyl-1,6-dimethyl-4-(2-nitrophenyl)-4,7-dihydropyrazolo[3,4-b]pyridine-5-carboxylate,
(6) 2-Cyclopentyloxyethyl 3-cyclopentyl-1,6-dimethyl-4-(2-nitrophenyl)-4,7-dihydropyrazolo[3,4-b]pyridine-5-carboxylate,
(7) 2-Cyclohexyloxyethyl 3-cyclopentyl-1,6-dimethyl-4-(2-nitrophenyl)-4,7-dihydropyrazolo[3,4-b]pyridine-5-carboxylate,
(8) 2-Tetrahydrofurylmethyl 3-cyclopentyl-1,6-dimethyl-4-(2-nitrophenyl)-4,7-dihydropyrazolo[3,4-b]pyridine-5-carboxylate,
(9) 2-Phenoxyethyl 3-cyclopentyl-1,6-dimethyl-4-(2-nitrophenyl)-4,7-dihydropyrazolo[3,4-b]pyridine-5-carboxylate,
(10) 2-Phenoxyethyl 3-cyclopentyl-1,6-dimethyl-4-(3-nitrophenyl)-4,7-dihydropyrazolo[3,4-b]pyridine-5-carboxylate,
(11) 2-Phenoxyethyl 3-cyclohexyl-1,6-dimethyl-4-(2-nitrophenyl)-4,7-dihydropyrazolo[3,4-b]pyridine-5-carboxylate,
(12) 2-Methylthioethyl 3-cyclopentyl-1,6-dimethyl-4-(2-nitrophenyl)-4,7-dihydropyrazolo[3,4-b]pyridine-5-carboxylate,
(13) 3-dimethylaminopropyl 3-cyclopentyl-1,6-dimethyl-4-(2-nitrophenyl)-4,7-dihydropyrazolo[3,4-b]pyridine-5-carboxylate,

(14) N-Benzylpyrrolidin-3-yl 3-cyclopentyl-1,6-dimethyl-4-(2-nitrophenyl)-4,7-dihydropyrazolo[3,4-b]pyridine-5-carboxylate,
(15) N-Benzylpiperidin-4-yl 3-cyclopentyl-1,6-dimethyl-4-(2-nitrophenyl)-4,7-dihydropyrazolo[3,4-b]pyridine-5-carboxylate,
(16) n-Pentyl 3-cyclopentyl-1,6-dimethyl-4-(2-nitrophenyl)-4,7-dihydropyrazolo[3,4-b]pyridine-5-carboxylate,
(17) Phenethyl 3-cyclopentyl-1,6-dimethyl-4-(2-nitrophenyl)-4,7-dihydropyrazolo[3,4-b]pyridine-5-carboxylate,
(18) 4-Chlorophenethyl 3-cyclopentyl-1,6-dimethyl-4-(2-nitrophenyl)-4,7-dihydropyrazolo[3,4-b]pyridine-5-carboxylate,
(19) 3,4-Dimethoxyphenethyl 3-cyclopentyl-1,6-dimethyl-4-(2-nitrophenyl)-4,7-dihydropyrazolo[3,4-b]pyridine-5-carboxylate,
(20) 1-Methoxy-2-phenylethyl 3-cyclopentyl-1,6-dimethyl-4-(3-nitrophenyl)-4,7-dihydropyrazolo[3,4-b]pyridine-5-carboxylate,
(21) 2-Isopropyl-4-methylcyclohexyl 3-cyclopentyl-1,6-dimethyl-4-(3-nitrophenyl)-4,7-dihydropyrazolo[3,4-b]pyridine-5-carboxylate,
(22) 2-Phenylthioethyl 3-cyclopentyl-1,6-dimethyl-4-(2-nitrophenyl)-4,7-dihydropyrazolo[3,4-b]pyridine-5-carboxylate,
(23) 2-Isopropylthioethyl 3-cyclopentyl-1,6-dimethyl-4-(2-nitrophenyl)-4,7-dihydropyrazolo[3,4-b]pyridine-5-carboxylate,
(24) 2-Cyclopentylthioethyl 3-cyclopentyl-1,6-dimethyl-4-(2-nitrophenyl)-4,7-dihydropyrazolo[3,4-b]pyridine-5-carboxylate,
(25) 2-Cyclopentylethyl 3-cyclopentyl-1,6-dimethyl-4-(2-nitrophenyl)-4,7-dihydropyrazolo[3,4-b]pyridine-5-carboxylate,
(26) Cyclohexylmethyl 3-cyclopentyl-1,6-dimethyl-4-(2-nitrophenyl)-4,7-dihydropyrazolo[3,4-b]pyridine-5-carboxylate,
(27) Cyclopentyl 3-cyclopentyl-1,6-dimethyl-4-(2-nitrophenyl)-4,7-dihydropyrazolo[3,4-b]pyridine-5-carboxylate, and
(28) Cyclohexyl 3-cyclopentyl-1,6-dimethyl-4-(2-nitrophenyl)-4,7-dihydropyrazolo[3,4-b]pyridine-5-carboxylate.

In addition, the acid addition salts, which can be obtained from the above-listed compounds, can be used as an active ingredient in this invention. Some examples of the acids capable to form such salts are inorganic acids such as hydrohalogenic acid (hydrochloric acid, hydrobromic acid or the like), sulfuric acid, nitric acid, phospholic acid or the like; and organic acids such as acetic acid, propionic acid, oxalic acid, malonic acid, succinic acid, glutaric acid, adipic acid, malic acid, maleic acid, fumaric acid, citric acid, benzoic acid, methanesulfonic acid or the like.

[Effect and Use]

The novel compounds of the present invention have the advantage that they have excellent antihypertensive and coronary vasodilating actions derived from Ca-blocking action, but have no systole inhibitory action which is one of adverse reactions and have been a defect of the conventional Ca-blockers. The biological tests of the following compounds were performed as explained below.

(Compounds Tested: Part 1)

(A): Nifedipine
(B-1): Methyl 3-cyclopentyl-1,6-dimethyl-4-(3-nitrophenyl)-4,7-dihydropyrazolo[3,4-b]pyridine-5-carboxylate
(C-1): Ethyl 3-cyclopentyl-1,6-dimethyl-4-(3-nitrophenyl)-4,7-dihydropyrazolo[3,4-b]pyridine-5-carboxylate hydrochloride (Compounds Tested: Part 2)

(A): Nifedipine
(B-2): 2-Methoxyethyl 3-cyclopentyl-1,6-dimethyl-4-(2-nitrophenyl)-4,7-dihydropyrazolo[3,4-b]pyridine-5-carboxylate
(C-2): 2-Methoxyethyl 3-cyclopentyl-1,6-dimethyl-4-(3-nitrophenyl)-4,7-dihydropyrazolo[3,4-b]pyridine-5-carboxylate
(D): 2-Methoxyethyl 3-cyclohexyl-1,6-dimethyl-4-(2-nitrophenyl)-4,7-dihydropyrazolo[3,4-b]pyridine-5-carboxylate
(E): 2-Methoxyethyl 3-cyclopentylmethyl-1,6-dimethyl-4-(2-nitrophenyl)-4,7-dihydropyrazolo[3,4-b]pyridine-5-carboxylate
(F): 3-Isopropoxypropyl 3-cyclopentyl-1,6-dimethyl-4-(2-nitrophenyl)-4,7-dihydropyrazolo[3,4-b]pyridine-5-carboxylate
(G): 2-Cyclopentyloxyethyl 3-cyclopentyl-1,6-dimethyl-4-(2-nitrophenyl)-4,7-dihydropyrazolo[3,4-b]pyridine-5-carboxylate
(H): 2-Tetrahydrofurylmethyl 3-cyclopentyl-1,6-dimethyl-4-(2-nitrophenyl)-4,7-dihydropyrazolo[3,4-b]pyridine-5-carboxylate
(I): 2-Phenoxyethyl 3-cyclopentyl-1,6-dimethyl-4-(2-nitrophenyl)-4,7-dihydropyrazolo[3,4-b]pyridine-5-carboxylate
(J): 2-Methylthioethyl 3-cyclopentyl-1,6-dimethyl-4-(2-nitrophenyl)-4,7-dihydropyrazolo[3,4-b]pyridine-5-carboxylate
(K): Phenethyl 3-cyclopentyl-1,6-dimethyl-4-(2-nitrophenyl)-4,7-dihydropyrazolo[3,4-b]pyridine-5-carboxylate
(L): 4-Chlorophenethyl 3-cyclopentyl-1,6-dimethyl-4-(3-nitrophenyl)-4,7-dihydropyrazolo[3,4-b]pyridine-5-carboxylate
(M): 3,4-Dimethoxyphenethyl 3-cyclopentyl-1,6-dimethyl-4-(3-nitrophenyl)-4,7-dihydropyrazolo[3,4-b]pyridine-5-carboxylate (Test Method)

(1) Antihypertensive Action:

Female Spontaneously Hypertensive Rats(-hereinafter referred to as SHR) with 160 mmHg of systolic pressure were employed without anaesthetization. The systolic pressure was, after SHRs were kept warm at 50° C. for 2 to 3 minutes, bloodlessly measured by the tail-cuff method [Japan J. Pharmacol., 28, 617 (1978)] using a Physiograph and an Electrosphygmomanometer (DMP-4B, PE-300, Narco Biosystems, Inc., Houston). Each compound was intraperitoneally administered to SHR at a dose of 3 mg per kilogramm.

(Result)

TABLE 1

(Part 1)

| Compounds | Maximum Hypotension (mmHg) | Duration of Effect (hours) |
|---|---|---|
| (A) | 45 | 6 |
| (B-1) | 66 | 16 |
| (C-1) | 42 | 14 |

(2) Coronary Vasodilating Action and Systole Inhibitory Action:

Guinea pigs with 400–800g of body weight were hit strongly on their heads and the cartoid artery of each Guinea pigs was cut down in order to make them bloodless. The heart was isolated and perfused with at a constant pressure (50 cm $H_2O$) by the Langendorff method [Basic Pharmacology & Therapeutics, 9(4), 181 (1981)]. Krebs-Ringer bicarbonate solution (27° C.) containing 0.5% defibrinated blood was employed as a perfusate, into which a mixed gas of 95% oxygen and 5% carbon dioxide was continuously introduced. The flowing perfusate was led into a drop counter, and the changes of the flow i.e. increase and decrease are regarded as the respective indications for coronary vasodilation and vasoconstriction. The isomeric contraction of apex and the number of drops of the coronary perfusate were recorded on a Recticorder (RJG 3006, Nihon Koden) by way of an F-D Pick-up (SB-IT, Nihon Koden). Each of the test compounds at a dose of 0.1 μg was administered through the short rubber tube connecting the aorta and the cannula.

(Results)

Antihypertensive action is shown in a maximal decrease of blood pressure, i.e. a maximum difference between systolic pressures after and before the administration of the test compound; along with which the duration period is also shown.

Coronary vasodilating action is shown in changes of the quantiy of the perfusate, and systole inhibitory action is shown in those of inotropic tension.

(Result)

TABLE 2

| | Coronary vasodilating action (Part 1) | | |
|---|---|---|---|
| | Perfusion Flow Change (%) | | |
| Compounds | 0.1 μg | 1 μg | 10 μg |
| (A) | +38 | +100 | |
| (B-1) | +26 | +73 | +180 |
| (C-1) | +40 | +79 | +93 |

TABLE 3

| | Negative inotropic action (Part 1) | | |
|---|---|---|---|
| | Change of Contractile Tension (%) | | |
| Compounds | 0.1 μg | 1 μg | 10 μg |
| (A) | −15 | −57 | |
| (B-1) | 0 | 0 | 0 |
| (C-1) | 0 | 0 | 0 |

TABLE 1

(Part 2)
Antihypertensive action, coronary vasodilating action and systole inhibitory action:

| Compound | Maximum Hypertension (mmHg) | Duration of Effect (hours) | Perfusion Flow Change (%) | Change of Contractile Tension (%) |
|---|---|---|---|---|
| (A) | 45 | 6 | +38 | −15 |
| (B-2) | 45 | 6 | +28 | 0 |
| (C-2) | 36 | 6 | +15 | 0 |
| (D) | 65 | 6 | +32 | 0 |
| (E) | 26 | 6 | +20 | 0 |
| (F) | 53 | 6 | +65 | 0 |
| (G) | 53 | 6 | +67 | 0 |
| (H) | 0 | — | +34 | 0 |
| (I) | 74 | 6 | +43 | 0 |
| (J) | 20 | 6 | +68 | 0 |
| (K) | 75 | 6 | +63 | 0 |
| (L) | 74 | 6 | — | — |
| (M) | 86 | 6 | — | — |

(3) Acute Toxicity:

In female DS mice (body weight: about 20g), $LD_{50}$ value after the intravenous administration of the compounds was calculated by the Brownlee's up and down method [J. Am. Sat. As., 48, 262 (1953)].

TABLE 4

(Part 1)

| Compounds | $LD_{50}$ (mg/kg) |
|---|---|
| (A) | 10.7 |
| (B-1) | 31.5 |
| (C-1) | 50.6 |

Since the compounds of this invention, as clearly seen from the above-listed results, show the highly antihypertensive and coronary vasodilating actions but no systole inhibitory action with low acute toxicity, they can be used as a cardiovascular agent with lesser adverse reactions to human or animals.

The compounds of this invention and the acid addition salts thereof can orally or parenterally be administered to human or animals and can be manufactured in various formulations in compliance with the usage. They, for instance, can be in a formulation of tablets, capsules, pills, granules, fine granules, aqueous solutions, emulsions or the like. In the course of the formulation, conventional carriers or diluents such as lactose, sucrose, starch, cellulose, talc, magnesium stearate, magnesium oxide, calcium sulfate, powdered gum arabic, gelatin, sodium arginate, sodium benzoate, stearic acid and the like are employed. Injections used may be in a formulation of a solution with distilled water, saline solution, Ringer solution or the like, or a suspension in sesame oil.

The compounds of this invention may be administered to an adult orally at a dose of about 1–50 mg a day, or intravenously at about 0.5–20 mg a day.

The present invention is further described in the following Examples and Preparations.

EXAMPLE 1 (Part 1)

Preparation of ethyl 3-cyclopentyl-1,6-dimethyl-4-(3-nitrophenyl)-4,7-dihydropyrazolo[3,4-b]pyridine-5-carboxylate

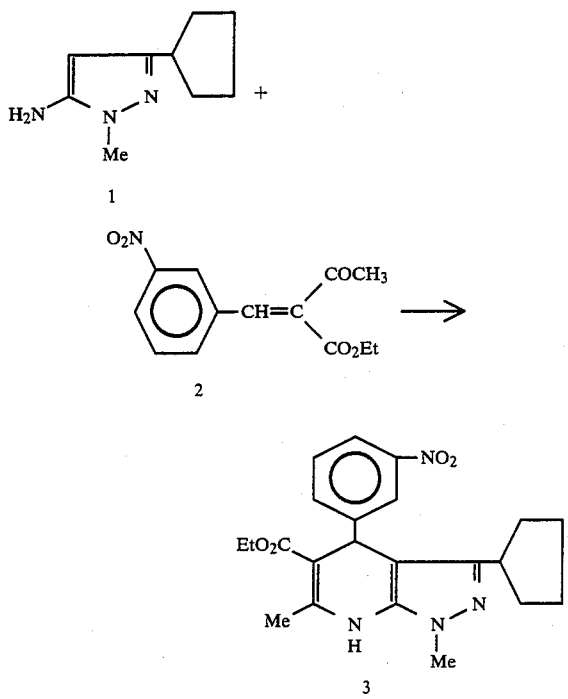

A mixture of 0.83 g (5 mmol) of 5-amino-3-cyclopentyl-1-methylpyrazole 1 and 1.32 g (5 mmol) of ethyl 3-nitrobenzylidene acetate 2 in 10 ml of t-butanol is heated at 80° C. under nitrogen gas for 3 days. The mixture is concentrated under reduced pressure, and the resulting residue is dissolved in chloroform, washed with an aqueous sodium bicarbonate solution and then with an aqueous sodium chloride solution. The solution is dried with magnesium sulfate and chromatographed on a column of silica gel. The chloroform-ethyl acetate (20:1) fraction gives 2 g of the objective compound as an yellow oily material.

IR: $\nu_{max}^{Nujol}$ 3270, 3150, 1690, 1350 cm$^{-1}$

NMR: $\delta^{CDCl_3}$ 1.17 (3H, t), 1.00–2.80 (9H, m), 2.38, 3.67 (3H×2, s), 4.03 (2H, q), 5.25 (1H, s), 7.13–8.10 (4H, m)

The objective compound (2 g) is converted into the hydrochloride on treatment with an ether-hydrochloric acid mixture, which is recrystallized from acetone to give 1.75 g of the hydrochloride. (Yield: 78.4%) m.p. 170°–173° C.

Elemental analysis

Calcd (%): C, 59.12; H, 6.09; N, 12.54 (for $C_{22}H_{26}N_4O_4 \cdot HCl$)

Found (%): C, 58.90; H, 6.10; N, 12.57

IR: $\nu_{max}^{Nujol}$ 2630, 2550, 1680, 1347 cm$^{-1}$

NMR: $\delta^{CDCl_3}$ 0.93–2.90 (9H, m), 1.17 (3H, t), 2.61 (3H, s) 4.03 (2H, q), 6.03 (1H), 5.22 (1H, s), 7.23–8.17 (4H, m)

EXAMPLES 2-42 (Part 1)

In the same manner as in Example 1, the compounds described in Table 5 can be prepared. Tables 6 and 7 show the data of each product, i.e. physical constants, elemental analysis, IR spectra, and NMR spectra.

TABLE 5

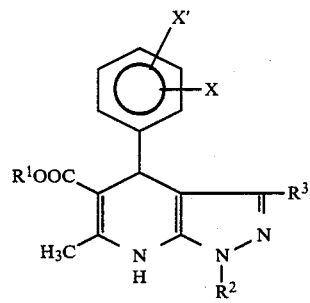

| Ex. | R$^1$ | R$^2$ | R$^3$ | X, X' | Yield (%) |
|---|---|---|---|---|---|
| 2 | C$_2$H$_5$ | CH$_3$ | H | 3-NO$_2$,H | 47.4 |
| 3 | CH$_3$ | " | " | 2-NO$_2$,H | 42.1 |
| 4 | " | " | i-C$_3$H$_8$ | 3-NO$_2$,H | 92.6* |
| 5 | " | " | n-C$_4$H$_9$ | " | 96.7 |

TABLE 5-continued
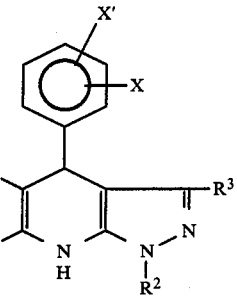
| Ex. | R¹ | R² | R³ | X, X' | Yield (%) |
|---|---|---|---|---|---|
| 6 | " | " |  | " | 68.5 |
| 7 | " | " | 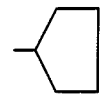 | 2-NO₂,H | 77.6 |
| 8 | " | " | " | 3-NO₂,H | 60.6 |
| 9 | i-C₃H₈ | " | " | " | 68.2* |
| 10 | C₂H₅ | " | " | 2-Cl,H | 59.0* |
| 11 | " | " | " | 2,6-Cl₂ | 15.7 |
| 12 | CH₃ | " | 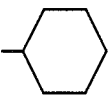 | 3-NO₂,H | 71.7* |
| 13 | " | " | 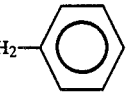 | " | 71.4* |
| 14 | C₂H₅ | H | 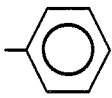 | " | 99.0 |
| 15 | " | 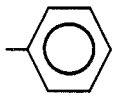 | " | " | 79.2 |
| 16 | CH₃ | CH₃ | 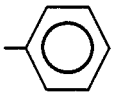 | 3-NO₂,H | 91.1 |
| 17 | C₂H₅ | " | " | " | 83.7 |
| 18 | CH₃ | " | " | 2-NO₂,H | 84.2 |
| 19 | C₂H₅ | " | 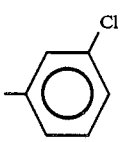 | 3-NO₂,H | 94.5 |
| 20 | CH₃ | " | 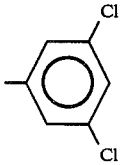 | " | 84.5 |

TABLE 5-continued

[Structure: dihydropyridine-pyrazole fused ring system with phenyl bearing X, X' substituents; R¹OOC, H₃C, NH on pyridine ring; R², R³ on pyrazole]

| Ex. | R¹ | R² | R³ | X, X' | Yield (%) |
|-----|-----|-----|-----|-------|-----------|
| 21 | C₂H₅ | " | " | " | 51.3 |
| 22 | " | " | 3-CF₃-C₆H₄ | " | 74.1 |
| 23 | " | " | 3-CN-C₆H₄ | " | 68.3 |
| 24 | " | " | 3-COOCH₃-C₆H₄ | " | 78.3 |
| 25 | " | " | 3-COOC₂H₅-C₆H₄ | " | 81.0 |
| 26 | " | " | 2-pyridyl | " | 75.7 |
| 27 | CH₃ | " | 2-furyl | " | 77.7 |
| 28 | " | " | COOCH₃ | " | 59.8 |
| 29 | C₂H₅ | " | COOC₂H₅ | " | 58.9 |
| 30 | CH₃ | " | COO—i-C₃H₈ | " | 56.5 |
| 31 | C₂H₅ | " | 4-OCH₃-C₆H₄ | " | 80.4 |
| 32 | CH₃ | cyclopentyl | cyclopentyl | " | 71.8 |
| 33 | " | CH₃ | i-C₄H₉ | " | 59.0 |
| 34 | " | " | t-C₄H₉ | " | 38.8 |
| 35 | " | " | n-C₅H₁₁ | " | 85.7* |

TABLE 5-continued

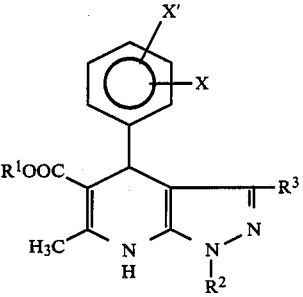

| Ex. | R¹ | R² | R³ | X, X' | Yield (%) |
|---|---|---|---|---|---|
| 36 | " | " | $-\underset{\underset{CH_3}{\mid}}{\overset{\overset{C_2H_5}{\mid}}{C}}-C_2H_5$ | " | 57.4* |
| 37 | " | " | (cyclopropyl) | " | 73.7 |
| 38 | " | " | (cyclohexyl) | 2-NO₂,H | 79.6 |
| 39 | " | " | (cyclohexyl) | 3-NO₂,H | 95.2 |
| 40 | " | " | (4-methylcyclohexyl) | " | 53.2 |
| 41 | " | " | (1-ethylcyclohexyl) | " | 59.6* |
| 42 | " | " | (1-methylimidazol-2-yl) | " | 76.8 |

*Hydrochloride

TABLE 6
(Part 1)

| | | | | | Elemental Analysis | | | | | |
|---|---|---|---|---|---|---|---|---|---|---|
| | Appear- | Solvent in | | | Calcd. | | | Found. | | |
| Ex. | ance* | Recrystallization | M.P. (°C.) | Molecular Formula | C | H | N | C | H | N |
| 2 | YP | Ethyl acetate | 153–154 | $C_{17}H_{18}N_4O_4$ | 59.64 | 5.30 | 16.37 | 59.68 | 5.25 | 16.33 |
| 3 | " | Isopropanol | 213–214 | $C_{16}H_{16}N_4O_4$ | 58.53 | 4.91 | 17.07 | 58.68 | 4.89 | 17.14 |
| 4 | " | Methanol | 214–220 | $C_{20}H_{24}N_4O_4 \cdot HCl$ | 57.21 | 5.76 | 13.34 | 56.93 | 5.97 | 13.36 |
| 5 | OP | Ether | 129–132 | $C_{20}H_{24}N_4O_4$ | 62.48 | 6.29 | 14.58 | 62.52 | 6.31 | 14.46 |
| 6 | YP | Ethyl acetate | 183–185 | $C_{20}H_{22}N_4O_4$ | 62.81 | 5.80 | 14.65 | 62.63 | 5.83 | 14.58 |
| 7 | " | Ethanol | 208–213 | $C_{21}H_{24}N_4O_4$ | 63.62 | 6.10 | 14.13 | 63.50 | 6.15 | 14.10 |
| 8 | " | Isopropyl ether | 172–173 | $C_{21}H_{24}N_4O_4$ | 63.62 | 6.10 | 14.13 | 63.42 | 6.08 | 14.07 |
| 9 | CP | Isopropanol | 170–190 (dec.) | $C_{23}H_{25}N_4O_4Cl \cdot HCl \cdot \frac{1}{2}H_2O$ | 59.29 | 5.84 | 12.03 | 59.72 | 6.31 | 12.03 |
| 10 | " | Methanol-Acetone | 160–170 (dec.) | $C_{22}H_{26}N_3O_2Cl \cdot HCl$ | 60.55 | 6.24 | 9.63 | 60.63 | 6.31 | 9.75 |
| 11 | " | Isopropyl ether | 146–148 | $C_{22}H_{25}N_3O_2Cl_2 \cdot \frac{1}{2}H_2O$ | 59.60 | 5.91 | 9.47 | 59.56 | 6.04 | 9.41 |
| 12 | YP | Methanol | 195–230 (dec.) | $C_{22}H_{26}N_4O_4 \cdot HCl$ | 59.13 | 6.09 | 12.54 | 58.76 | 6.09 | 12.50 |

TABLE 6-continued
(Part 1)

| Ex. | Appearance* | Solvent in Recrystallization | M.P. (°C.) | Molecular Formula | Elemental Analysis Calcd. C | H | N | Found C | H | N |
|---|---|---|---|---|---|---|---|---|---|---|
| 13 | CP | Methylene chloride-Ether | 124–126 | $C_{23}H_{22}N_4O_4 \cdot HCl \cdot \frac{1}{2}H_2O$ | 59.54 | 5.22 | 12.07 | 59.35 | 5.36 | 11.83 |
| 14 | YP | Benzene | 233–234 | $C_{22}H_{20}N_4O_4$ | 65.33 | 4.99 | 13.86 | 65.23 | 4.83 | 13.93 |
| 15 | " | Ethyl acetate | 214–215 | $C_{28}H_{24}N_4O_6$ | 69.99 | 5.03 | 11.66 | 70.28 | 5.09 | 11.68 |
| 16 | OP | " | 209–210 | $C_{22}H_{20}N_4O_4$ | 65.23 | 4.99 | 13.86 | 65.42 | 4.91 | 13.89 |
| 17 | YN | Methylene chloride-Ether | 157–158 | $C_{23}H_{22}N_4O_4$ | 66.01 | 5.30 | 13.39 | 65.94 | 5.16 | 13.33 |
| 18 | OP | Chloroform | 205–206 | $C_{22}H_{20}N_4O_4 \cdot \frac{1}{2}H_2O$ | 63.91 | 5.12 | 13.55 | 64.17 | 5.06 | 13.64 |
| 19 | YP | Ethanol | 214–216 | $C_{23}H_{21}N_4O_4Cl$ | 61.00 | 4.67 | 12.37 | 61.03 | 4.43 | 12.38 |
| 20 | " | Tetrahydrofuran-Ethanol | 263–264 | $C_{22}H_{18}N_4O_4Cl_2$ | 55.82 | 3.83 | 11.84 | 55.80 | 3.82 | 11.74 |
| 21 | " | Methylene chloride-Ether | 222–224 | $C_{23}H_{20}N_4O_4Cl_2$ | 56.68 | 4.14 | 11.50 | 56.32 | 4.22 | 11.43 |
| 22 | " | Methanol | 217–218 | $C_{24}H_{21}N_4O_4F_3$ | 59.25 | 4.35 | 11.52 | 59.31 | 4.39 | 11.56 |
| 23 | YN | " | 211–214 | $C_{24}H_{21}N_5O_4$ | 65.00 | 4.77 | 15.79 | 64.87 | 4.89 | 15.67 |
| 24 | OP | Ethanol | 182–183 | $C_{25}H_{24}N_4O_6$ | 63.01 | 5.08 | 11.76 | 62.93 | 5.11 | 11.80 |
| 25 | YN | Methanol | 225–227 | $C_{26}H_{26}N_4O_6$ | 63.66 | 5.34 | 11.42 | 63.42 | 5.36 | 11.39 |
| 26 | YP | Isopropanol | 213–214 | $C_{22}H_{21}N_5O_4$ | 63.00 | 5.05 | 16.70 | 63.16 | 4.94 | 16.63 |
| 27 | " | Ethanol | 195–198 | $C_{20}H_{18}N_4O_5$ | 60.91 | 4.60 | 14.21 | 60.85 | 4.70 | 14.08 |
| 28 | " | Ethyl acetate | 206–209 | $C_{18}H_{18}N_4O_6$ | 55.95 | 4.70 | 14.50 | 55.91 | 4.71 | 14.40 |
| 29 | YN | " | 133–135 | $C_{20}H_{22}N_4O_6$ | 57.96 | 5.35 | 13.52 | 57.29 | 5.34 | 12.97 |
| 30 | YP | " | 180–182 | $C_{20}H_{22}N_4O_6$ | 57.96 | 5.35 | 13.52 | 57.73 | 5.36 | 13.30 |
| 31 | " | " | 159–161 | $C_{24}H_{24}N_4O_4$ | 64.27 | 5.39 | 12.49 | 64.33 | 5.42 | 12.48 |
| 32 | OP | Ethanol | 175–177 | $C_{25}H_{30}N_4O_4$ | 66.66 | 6.71 | 12.44 | 66.68 | 6.68 | 12.44 |
| 33 | YP | Ethyl acetate | 110–115 | $C_{20}H_{24}N_4O_4$ | 62.48 | 6.29 | 14.58 | 62.12 | 6.12 | 14.76 |
| 34 | " | " | 153–154 | $C_{20}H_{24}N_4O_4 \cdot \frac{1}{2}H_2O$ | 61.06 | 6.40 | 14.24 | 61.25 | 6.52 | 13.88 |
| 35 | " | Ethanol | 140–155 | $C_{21}H_{26}N_4O_4 \cdot HCl$ | 58.00 | 6.26 | 12.88 | 58.03 | 6.37 | 12.71 |
| 36 | CP | Acetone | 172–175 | $C_{22}H_{28}N_4O_4 \cdot HCl$ | 58.86 | 6.51 | 12.48 | 58.59 | 6.47 | 12.46 |
| 37 | YP | Ethyl ether | 100–102 | $C_{19}H_{20}N_4O_4$ | 61.94 | 5.47 | 15.21 | 61.84 | 5.56 | 15.05 |
| 38 | " | Methyl cyanide | 215–219 | $C_{22}H_{26}N_4O_4$ | 64.37 | 6.39 | 13.65 | 64.21 | 6.31 | 13.52 |
| 39 | " | Ethyl ether | 199–200 | $C_{23}H_{28}N_4O_4$ | 65.07 | 6.65 | 13.20 | 65.13 | 6.77 | 13.10 |
| 40 | " | Isopropanol | 197–198 | $C_{23}H_{28}N_4O_4$ | 65.07 | 6.65 | 13.20 | 65.09 | 6.60 | 13.05 |
| 41 | PL | Ethanol | 175–176 | $C_{24}H_{30}N_4O_4 \cdot HCl$ | 60.69 | 6.58 | 11.80 | 60.35 | 6.43 | 11.77 |
| 42 | YN | Methanol | 207–208 (dec.) | $C_{20}H_{20}N_6O_4 \cdot CH_3OH$ | 57.00 | 5.92 | 19.00 | 57.10 | 5.48 | 19.05 |

*YP = Yellow prisms, CP = Colorless prisms, OP = Orange prisms, YN = Yellow needles, PL = Colorless plates

TABLE 7
(Part 1)

| Ex. | IR ($\nu_{max}^{cm-1}$) NH | CO | $NO_2$ | NMR ($\delta^{CDCl_3}$) |
|---|---|---|---|---|
| 2 | 3340 | 1690 | 1343 | 1.10(3H,t), 2.45(3H,s), 3.70(3H,s), 4.00(2H,q), 5.30(1H,s), 7.00(1H,s), 7.20(1H,bs), 7.30–8.10(4H,m) |
| 3 | 3280 3175 | 1680 | 1350 | 2.45(3H,s), 3.40(3H,s), 3.70(3H,s), 5.70(1H,s), 6.80(1H,bs), 7.30–7.85(4H,m) |
| 4 | 3430 3290 | 1690 | 1350 | 0.90(3H,d), 1.10(3H,d), 1.20(3H,t), 2.40(3H,s), 2.20–2.80(1H,m), 3.70(3H,s), 4.05(2H,m), 5.30(1H,s), 6.90(1H,bs), 7.35–8.10(4H,m) |
| 5 | 3350 | 1693 | 1345 | 0.53–1.53(7H,m), 2.20(2H,m), 2.40(3H,s), 3.59(3H,s), 3.68(3H,s), 5.25(1H,s), 7.44(1H,bs), 7.23–8.13(4H,m) |
| 6 | 3375 | 1705 | 1350 | 2.10–3.07(7H,m), 2.37(3H,s), 3.56(3H,s), 3.65(3H,s), 5.16(1H,s), 7.37–7.90(5H,m) |
| 7 | 3290 | 1673 | 1353 | 0.87–3.10(9H,m), 2.32(3H,s), 3.32(3H,s), 3.67(3H,s), 5.62(1H,s), 7.10–14 7.83(4H,m) |
| 8 | 3375 | 1700 | 1380 | 1.17–2.83(9H,m), 2.27(3H,s), 3.58(3H,s), 3.67(3H,s), 5.25(1H,s), 6.70(1H,bs), 7.27–8.10(4H,m) |
| 9 | 2560 | 1693 | 1353 | *1.03(3H,d), 1.25(3H,d), 1.53–2.60(9H,m), 2.38(3H,s), 3.65(3H,s), 4.90(2H,q), 5.23(1H,s), 7.40–7.93(5H,m) |
| 10 | 2360 | 1701 | | *1.17(3H,t), 1.60–2.80(9H,m), 2.38(3H,s), 3.52(3H,s), 4.02(2H,q), 5.62(1H,s), 7.13–8.10(5H,m) |
| 11 | 3470 3280 | 1670 | | 1.07(3H,t), 0.80–3.27(9H,m), 2.30(3H,s), 3.57(3H,s), 3.99(2H,q), 6.08(1H,s), 6.90–7.80(5H,m) |
| 12 | 2495 | 1699 | 1352 | *0.77–2.57(11H,m), 2.42(3H,s), 3.62(3H,s), 3.70(3H,s), 5.30(1H,s), 7.26(1H,bs), 7.43–8.02(3H,m) |
| 13 | 3200 | 1690 | 1350 | 2.30(3H,s), 3.52(3H,s), 3.60(5H,s), 5.00(1H,s), 6.73–8.23(4H,m) |
| 14 | 3200 3110 | 1705 | 1347 | **1.15(3H,t), 2.50(3H,s), 4.03(2H,q), 6.17(1H,bs), 6.45(1H,s), 7.10–8.17(9H,m), 10.33(1H,bs) |
| 15 | 3360 | 1698 | 1345 | **1.13(3H,t), 2.43(3H,t), 4.02(2H,q), 5.62(1H,s), 6.90(1H,bs), 7.13–8.03(9H,m) |
| 16 | 3350 | 1665 | 1373 | **2.42(3H,s), 3.50(3H,s), 3.80(3H,s), 5.52(1H,s), 7.03–7.93(14H,m), 9.57(1H,bs) |
| 17 | 3280 | 1678 | 1350 | 1.18(3H,t), 2.49(3H,s), 3.77(3H,s), 4.07(2H,q), 5.50(1H,s), 6.78(1H,bs), 7.13–8.03(9H,m) |
| 18 | 3315 | 1675 | 1375 | 2.32(3H,s), 3.35(3H,s), 3.80(3H,s), 6.05(1H,s), 7.07–7.77(9H,m), 9.60(1H,bs) |
| 19 | 3340 | 1690 | 1346 | 1.20(3H,t), 2.45(3H,s), 3.80(3H,s), 4.10(2H,q), 5.50(1H,s), 6.55(1H,bs), 7.10–8.10(9H,m) |
| 20 | 3355 | 1683 | 1350 | 2.40(3H,s), 3.53(3H,s), 3.83(3H,s), 5.47(1H,s), 7.20–8.00(8H,m), 9.60(1H,bs) |
| 21 | 3350 | 1692 | 1350 | 1.25(3H,s), 2.43(3H,s), 3.80(3H,s), 4.12(2H,q), 5.48(1H,s), 7.03–810(7H,m) |
| 22 | 3340 | 1692 | 1348 | 1.22(3H,t), 2.45(3H,s), 3.80(3H,s), 4.08(2H,q), 5.50(1H,s), 6.45(1H,bs), 7.17–8.02(7H,m) |

TABLE 7-continued
(Part 1)

| Ex. | IR ($\nu_{max}^{cm-1}$) NH | CO | NO$_2$ | NMR ($\delta^{CDCl_3}$) |
|---|---|---|---|---|
| 23 | 3350 | 1692 | 1348 | 1.20(3H,t), 2.45(3H,s), 3.82(3H,s), 4.07(2H,q), 5.50(1H,s), 7.12(1H,bs), 7.18-8.05(8H,m) |
| 24 | 3330 | 1723 1694 | 1343 | 1.22(3H,t), 2.43(3H,s), 3.80(3H,s), 3.93(3H,s), 4.09(2H,q), 5.60(1H,s), 7.18(1H,bs), 7.12-8.22(8H,m) |
| 25 | 3270 | 1712 1668 | 1350 | 1.20(3H,t), 1.40(3H,t), 2.47(3H,s), 3.83(3H,s), 4.09(2H,q), 4.40(2H,q), 5.60(1H,s), 6.60(1H,bs), 7.07-8.23(8H,m) |
| 26 | 3360 | 1695 | 1355 | 1.20(3H,t), 2.45(3H,s), 3.70(3H,s), 4.05(2H,q), 5.80(1H,s), 6.80(1H,bs), 7.00-8.70(8H,m) |
| 27 | 3360 | 1701 | 1350 | 2.39(3H,s), 3.64(3H,s), 3.74(3H,s), 5.36(1H,s), 6.50-8.63(8H,m) |
| 28 | 3320 | 1725 1700 | 1355 | 2.39(3H,s), 3.58(3H,s), 3.75(3H,s), 3.78(3H,s), 5.50(1H,s), 7.26-7.88(7H,m), 7.60(1H,bs) |
| 29 | 3220 3120 | 1735 1693 | 1350 | 1.20(3H,t), 1.30(3H,t), 2.42(3H,s), 3.80(3H,s), 4.07(2H,q), 4.29(2H,q), 5.58(1H,s), 7.45(1H,bs), 7.18-8.15(4H,m) |
| 30 | 3370 | 1725 1693 | 1350 | 1.20(3H,d), 1.32(3H,d), 2.38(3H,s), 3.63(3H,s), 3.78(3H,s), 5.17(1H,m), 5.58(1H,s), 7.35-8.02(4H,m), 8.07(1H,bs) |
| 31 | 3290 | 1630 | 1350 | 1.18(3H,t), 2.43(3H,s), 3.77(6H,s), 4.07(2H,q), 5.50(1H,s), 6.67-8.07(9H,m) |
| 32 | 3350 | 1695 | 1340 | 1.22-2.20(16H,m), 2.40(3H,s), 2.62(1H,m), 3.58(3H,s), 4.35(1H,m), 5.25(1H,s), 4.35(1H,bs), 7.30-8.13(4H,m) |
| 33 | 3220 | 1690 | 1347 | 0.70, 0.84(6H,d), 1.82(3H,m), 2.40, 3.57, 3.67(9H,s), 5.20(1H,s), 7.08(1H,bs), 7.62(4H,m) |
| 34 | 3300 | 1700 | 1350 | 1.08(9H,s), 2.42, 3.72, 3.78(9H,s), 5.45(1H,s), 6.57(1H,bs), 7.67(4H,m) |
| 35 | 2560 | 1701 | 1347 | 0.53-1.62(9H,m), 2.22(2H,m), 2.37, 3.55, 3.63(9H,s), 5.20(1H,s), 7.12-8.20(4H,m), 2.73(1H,bs) |
| 36 | 2640 | 1710 | 1350 | 0.33, 0.58(6H,d), 1.07, 2.34, 3.68, 3.73(12H,s), 1.49(4H,m), 5.32(1H,s), 7.13(1H,bs), 7.65(4H,m) |
| 37 | 3225 | 1695 | 1350 | 0.27-1.67(5H,m), 2.40, 3.57, 3.60(9H,s), 5.28(1H,s), 7.02(1H,bs), 7.15-8.07(4H,m) |
| 38 | 3320 | 1685 | 1360 | 0.70-2.87(11H,m), 2.37, 3.50, 3.67(9H,s), 5.87(1H,s), 7.12(1H,bs), 7.00-7.83(4H,m) |
| 39 | 3355 | 1700 | 1350 | 1.07-2.62(13H,m), 2.40, 3.58, 3.67(9H,s), 5.25(1H,s), 6.97(1H,bs), 7.28-8.12(4H,m) |
| 40 | 3340 | 1695 | 1340 | 0.70-2.35(10H,m), 0.84(3H,d), 2.41, 3.59, 3.68(9H,s), 5.27(1H,s), 6.79(1H,bs) 7.30-8.15(4H,m) |
| 41 | 2600 | 1666 | 1344 | 0.33(3H,t), 0.73-2.53(12H,m), 2.36, 3.68, 3.73(9H,s), 5.30(1H,s), 6.88(1H,bs), 7.11-8.01(4H,m) |
| 42 | | 1667 | 1347 | 2.65, 3.18, 3.44, 3.60(12H,s), 5.38(1H,s), 6.82-7.88(6H,m), 8.65(1H,bs) |

*Free base
**in DMSO-d$_6$

EXAMPLE 43 (Part 1)

Component (Tablet)

| | |
|---|---|
| Ethyl 3-cyclopentyl-1,6-dimethyl-4-(3-nitrophenyl)-4,7-dihydropyrazolo-[3,4-b]pyridine-5-carboxylate | 10 mg |
| Corn starch | 50 mg |
| Gelatin | 7.5 mg |
| Avicel (microcrystalline cellulose) | 25 mg |
| Magnesium stearate | 2.5 mg |
| Total | 95 mg |

The above composition is formulated into one tablet.

Reference example 1 (Part 1)

(i) Preparation of 5-amino-3-isopropyl-1-methylpyrazole

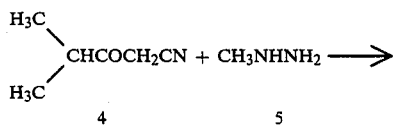

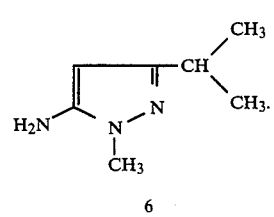

A mixture of 8.0 g (72 mmol) of 1-cyano-3-methyl-2-butanone 4 and 3.4 g (73.8 mmol) of methylhydrazine 5 in 2 ml of ethanol is stirred at room temperature for an hour, and concentrated under reduced pressure. The resulting residue is chromatographed on silica gel. The chloroform fraction is recrystallized from carbon tetrachloride to give 8.48 g (84.6% yield) of the titled compound as colorless prisms.

m.p. 111°-112° C.

NMR: $\delta^{CDCl_3}$ 1.20 (6H, d), 2.60-3.10 (1H, m), 3.40 (2H, bs), 3.60 (3H, s), 5.30 (1H, s)

(ii) Preparation of 1-cyano-3-methyl-2-butanone

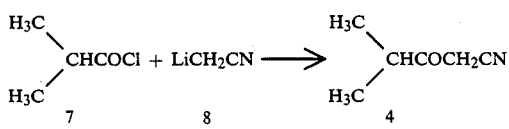

To a solution (100 ml) of 0.2 mol of n-butyllithium in anhydrous tetrahydrofuran is added dropwise a solution of 8.2 g (0.2 mmol) of acetonitrile in 12 ml of tetrahydrofuran under nitrogen gas at −70° C. within 30 minutes; after 2 hours, a solution of 10.65 g (0.1 mmol) of isobutyrylchloride in 18 ml of tetrahydrofuran is added dropwise thereto. After an hour, the reaction mixture is acidified with 10% hydrochloric acid and extracted with ether, and the extract is washed with an aqueous sodium chloride solution, dried with magnesium sulfate, and evaporated. The residue is distilled to give 8.05 g (72.5% yield) of the objective compound.

m.p. 62°-65° C.

NMR: δ$^{CDCl_3}$ 1.2 (6H, d), 2.6–3.1 (1H, m), 3.5 (2H, m)

Reference examples 2–19 (Part 1)

In the same manner as in Reference example 1, the compounds described in Table 8 can be prepared.

TABLE 8

| Ref. Ex. | R² | R³ | Yield (%) | M.P. (°C.) | NMR (δCDCl₃) |
|---|---|---|---|---|---|
| 2 | CH₃ | n-C₄H₉ | 89.1 | | 0.70–2.00(7H,m), 2.60(2H,t), 3.54(3H,s), 5.29(1H,s) |
| 3 | " | cyclopropyl | 68.2 | 117–118 | 1.50–3.33(7H,m), 3.54(3H,s), 3.60(2H,bs), 5.38(1H,s) |
| 4 | " | cyclopentyl | 74.4 | 149–150 | 1.33–2.20(8H,m), 2.60–3.10(1H,m), 3.57(5H,s), 5.32(1H,s) |
| 5 | " | cyclohexyl | 71.7 | 173–174 | 0.90–2.77(11H,m), 3.43(2H,bs), 3.57(3H,s), 5.32(1H,s) |
| 6 | " | CH₂–C₆H₅ | 89.2 | 130–131 | 3.40(2H,bs), 3.53(3H,s), 3.78(2H,s), 5.22(1H,s), 7.23(5H,s) |
| 7 | H | C₆H₅ | 94.3 | 110–111 | 4.75(2H,bs), 5.80(1H,s), 7.10–7.77(5H,m) |
| 8 | C₆H₅ | " | 78.0 | 130–131 | 5.83(1H,s), 7.20–7.80(5H,m) |
| 9 | CH₃ | " | 92.4 | 130–131 | 3.58(3H,s), 3.50(2H,bs), 5.73(1H,s), 7.15–7.78(5H,m) |
| 10 | " | 3-Cl-C₆H₄ | 31.0 | 127–128 | 3.65(3H,s), 5.80(1H,s), 7.10–7.80(4H,m) |
| 11 | " | 2,4-Cl₂-C₆H₃ | 99.1 | 155–156 | 3.63(3H,s), 3.63(2H,bs), 5.72(1H,s), 7.07–7.67(3H,m) |
| 12 | " | 3-CF₃-C₆H₄ | 62.2 | 91–92 | 3.58(2H,bs), 3.68(3H,s), 5.85(1H,s), 7.30–8.07(4H,m) |
| 13 | " | 3-CN-C₆H₄ | 79.1 | 179–181 | 3.55(2H,bs), 3.69(3H,s), 5.81(1H,s), 7.48–7.85(4H,m) |

TABLE 8-continued

| Ref. Ex. | R² | R³ | Yield (%) | M.P. (°C.) | NMR (δCDCl₃) |
|---|---|---|---|---|---|
| 14 | " | 3-(COOCH₃)-phenyl | 76.8 | 101–102 | 3.63(2H,bs), 3.68(3H,s), 3.90(3H,s), 5.88(1H,s), 7.42–8.37(4H,m) |
| 15 | CH₃ | 3-(COOC₂H₅)-phenyl | 77.9 | 113–114 | 1.38(3H,t), 3.62(2H,bs), 3.68(3H,s), 4.38(2H,q), 5.88(1H), 7.40–8.36(4H,m) |
| 16 | " | 2-pyridyl | 53.5 | 186–187 | 3.65(2H,bs), 3.70(3H,s), 6.15(1H,s), 7.00–8.00(4H,m) |
| 17 | " | 2-furyl | 14.2 | 118–120 | 3.52(2H,bs), 3.65(3H,s), 5.63(1H,s), 6.68–7.69(3H,m) |
| 18 | " | 4-methoxyphenyl | 75.1 | 140–141 | 3.65(3H,s), 3.78(3H,s), 5.75(1H,s), 6.73–7.67(4H,m) |
| 19 | cyclopentyl | cyclopentyl | 71.5 | 92–93 | 1.2–2.33(16H,m), 2.97(1H,m), 3.42(2H,bs), 4.35(1H,m), 5.33(1H,s) |

Reference example 20 (Part 1)

Preparation of ethyl 5-amino-1-methylpyrazole-3-carboxylate

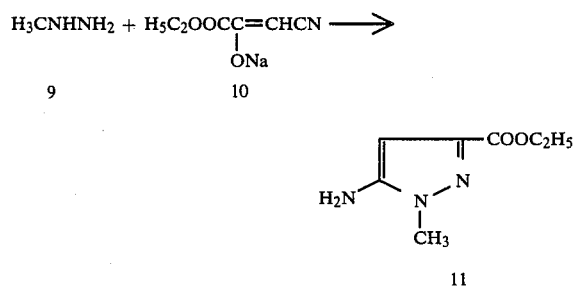

A mixture of 10 g (61.3 mmol) of the sodium salt of ethyl 3-cyanopyruvate 10 and 9.0 g (61.3 mmol) of methylhydrazine sulfate 9 in 100 ml of methanol is stirred at room temperature for 3 days, and then concentrated under reduced pressure. To the resulting residue are added an aqueous sodium bicarbonate solution and an aqueous sodium chloride solution, and the mixture is extracted 6 times with chloroform, dried with magnesium sulfate, and chromatographed on a column of silica gel. The ethyl acetate eluate gives 6.54 g (62.9% yield) of the objective compound 11 as an yellow oil.

NMR: $\delta^{CDCl_3}$ 1.35 (3H, t), 3.71 (3H, s), 3.76 (2H, bs), 4.35 (2H, q), 6.03 (1H, s)

Reference example 21 (Part 1)

Preparation of methyl 5-amino-1-methylpyrazole-3-carboxylate

To a solution of 48 mg (2.1 mmol) of sodium in 40 ml of methanol is added 2.0 mg (11.8 mmol) of 5-amino-3-ethoxycarbonyl-1-methylpyrazole, and the mixture is refluxed over night, and distilled under reduced pressure. To the resulting residue are added a small amount of water and sodium chloride, and the mixture is extracted 6 times with chloroform. The extract is dried with magnesium sulfate, chromatographed on a column of silica gel and eluted with ethyl acetate to give 1.37 g (74.1% yield) of the objective compound.

m.p. 101°–102° C.

NMR: $\delta^{CDCl_3}$ 3.71 (3H, s), 3.86 (3H, s), 3.90 (2H, bs), 6.05 (1H, s)

Reference example 22 (Part 1)

Preparation of isopropyl 5-amino-1-methylpyrazole-3-carboxylate

In the same manner as in Reference example 19. the titled compound can be prepared. (Yield: 72.9%)

m.p. 86°–87° C.

NMR: $\delta^{CDCl_3}$ 1.37 (6H, d), 3.72 (3H, s), 3.75 (2H, bs), 5.23 (1H, m)

Reference example 23 (Part 1)

Preparation of methyl 2-nitrobenzylidene acetate

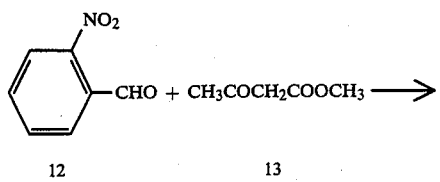

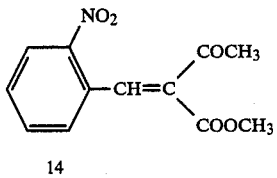

To 40 ml of benzene are added 11.6 g (0.1 mol) of methyl acetoacetate 13, 15 g (0.1 mol) of 2-nitrobenzaldehyde 12, 3 ml of acetic acid, and 0.8 ml of piperidine, and the mixture is kept at room temperature for 3 days, after which is added 12 g (0.1 mol) of magnesium sulfate thereto. The reaction mixture is stirred for 4 days, and filtered. Benzene is distilled off, and the residue is recrystallized from ethanol to give 22.5 g (90.0% yield) of the objective compound 14 as colorless prisms. m.p. 100°–101° C.

NMR: $\delta^{CDCl_3}$ 2.47 (3H, s), 3.60 (3H, s), 7.23–8.37 (4H, m)

EXAMPLE 1 (Part 2)

Preparation of 2-methoxyethyl 3-cyclopentyl-1,6-dimethyl-4-(2-nitrophenyl)-4,7-dihydropyrazolo[3,4-b]pyridine-5-carboxylate 3

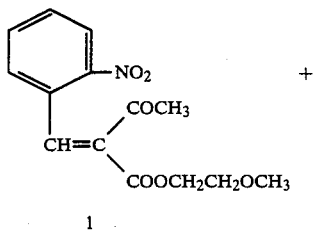

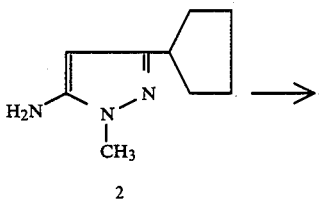

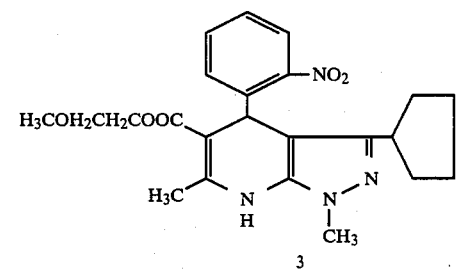

In 6 ml of tert-butanol are dissolved 0.90 g (3.05 mMol.) of 2-methoxyethyl 2-nitrobenzylideneacetoacetate 1 and 0.50 g (3.05 mMol.) of 3-cyclopentyl-5-amino-1-methylpyrazole 2, and the solution is allowed to react at 80° C. for 3 hours, then evaporated under reduced pressure. The resulting residue is crystallized from ether, filtered and washed with a small amount of ether to give the 1.15 g of the titled compound 3. This is recrystallized from ethanol to give 0.92 g of yellow prisms in 59.6% yield, mp. 196°–198° C.

Elementary Analysis: Calcd. (%) for $C_{23}H_{28}N_4O_5$: C, 62.71; H, 6.41; N, 12.72. Found (%): C, 62.69; H, 6.20; N, 12.82. IR(Nujol) $\nu$ max: 3260(NH), 1690(C=O), 1360(NO$_2$) cm$^{-1}$. NMR(CDCl$_3$) $\delta$ ppm: 0.97–2.03 (8H, m), 2.33, 3.27, 3.63 (3H×3, s), 2.92 (1H, m), 3.51 (2H, m), 4.13 (2H, m), 5.92 (1H, s), 6.67 (1H, br, s), 7.00–7.73 (4H, m).

EXAMPLES 2–33 (Part 2)

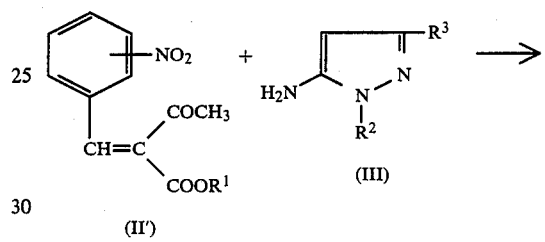

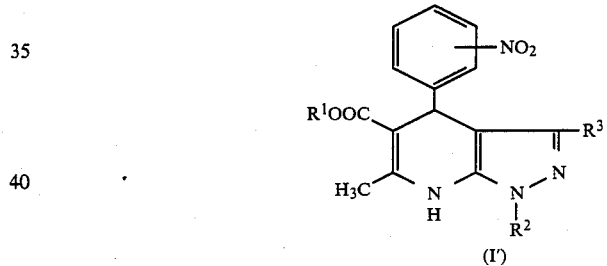

wherein $R^1$, $R^2$ and $R^3$ each has the same meaning as defined above.

A solution of compounds (II') and (III) in a solvent is allowed to react in nitrogen atmosphere at room temperature or under heating and then evaporated. The residue is crystallized from ether, or chromatographed on silica gel to give the objective compound (I'). This is, if needed, purified by recrystallization.

The objective compounds of the present invention can, which are listed in the following Table 2 (Part 2), be prepared in the manner commonly described above. Details of the reaction conditions are summarized in Table 3 (Part 2). Additionally, recrystallization solvents, appearance (crystal form, color), molecular formula and the result by elemental analysis in each compound or the acid addition salt are summarized in Table 4 (Part 2); and the IR- and NMR-spectrum data are shown in Table 5 (Part 2).

TABLE 2
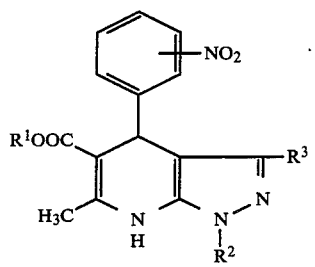
(I')
| Example No. | R¹ | R² | R³ | Position of —NO₂ | Yield (%) |
|---|---|---|---|---|---|
| 2 | —CH₂CH₂OCH₃ | —CH₃ | cyclopentyl | 3 | 97.5 |
| 3 | " | " | cyclohexyl | 2 | 72.1 |
| 4 | " | " | —CH₂-cyclopentyl | " | 51.5 |
| 5 | —CH₂CH₂CH₂OCH(CH₃)₂ | " | cyclopentyl | " | 75.4 |
| 6ª | —CH₂CH₂O-cyclopentyl | " | " | " | 77.0 |
| 7ª | —CH₂CH₂O-cyclohexyl | " | " | " | 78.9 |
| 8 | —CH₂-(tetrahydrofuran) | " | " | " | 81.5 |
| 9ᵇ | —CH₂CH₂O-phenyl | " | " | " | 81.9 |
| 10ª | " | " | " | 3 | 89.7 |
| 11ª | " | " | cyclohexyl | 2 | 81.7 |
| 12ᵇ | —CH₂CH₂SCH₃ | " | cyclopentyl | " | 31.5 |
| 13ᵇ | —CH₂CH₂CH₂N(CH₃)₂ | " | " | " | 42.3 |

TABLE 2-continued
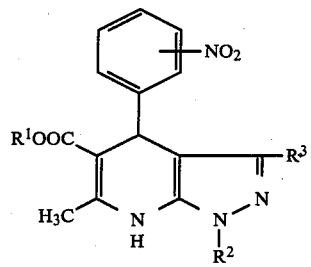
(I')
| Example No. | R¹ | R² | R³ | Position of —NO₂ | Yield (%) |
|---|---|---|---|---|---|
| 14 | ![pyrrolidine-CH2-phenyl] | " | " | " | 60.7 |
| 15[b] | ![piperidine-CH2-phenyl] | " | " | " | 54.7 |
| 16[a] | —(CH₂)₄.CH₃ | " | " | " | 72.8 |
| 17 | —CH₂CH₂-phenyl | " | " | " | 67.2 |
| 18[a] | —CH₂CH₂-C₆H₄-Cl | —CH₃ | cyclopentyl | 2 | 76.0 |
| 19[a] | —CH₂CH₂-C₆H₃(OCH₃)₂ | " | " | " | 74.8 |
| 20 | —CH(OCH₃)CH₂-phenyl | " | " | 3 | 96.2 |
| 21[a] | menthyl | " | " | " | 75.9 |
| 22[a] | —CH₂CH₂S-phenyl | " | " | 2 | 71.4 |
| 23[a] | —CH₂CH₂S—CH(CH₃)₂ | " | " | " | 77.5 |

TABLE 2-continued (I')

Structure: dihydropyridine fused with pyrazole bearing nitrophenyl, R¹OOC, CH₃, R², R³ substituents

| Example No. | R¹ | R² | R³ | Position of —NO₂ | Yield (%) |
|---|---|---|---|---|---|
| 24[a] | —CH₂CH₂—S—cyclopentyl | " | " | " | 77.8 |
| 25[a] | —CH₂CH₂—cyclopentyl | " | " | " | 72.8 |
| 26[a] | —CH₂—cyclohexyl | " | " | " | 76.8 |
| 27[a] | cyclopentyl | " | " | " | 67.0 |
| 28[a] | cyclohexyl | " | " | " | 64.3 |
| 29[a] | —CH₂CH₂CH₂—C₆H₄—Cl (4-Cl) | " | " | 3 | 73.2 |
| 30[a] | —CH₂CH₂CH₂—C₆H₃(OMe)₂ | " | " | " | 56.6 |
| 31[a] | —CH₂CH₂CH₂—C₆H₃Cl₂ (3,4-diCl) | " | " | " | 58.2 |
| 32[a] | —CH₂CH₂CH₂—C₆H₄—Br (4-Br) | " | " | " | 70.8 |

TABLE 2-continued

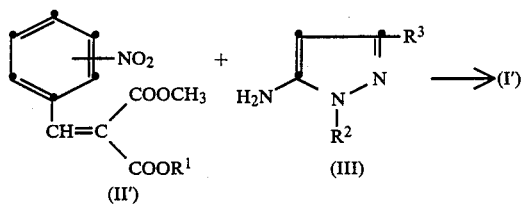
(I')

| Example No. | R¹ | R² | R³ | Position of —NO₂ | Yield (%) |
|---|---|---|---|---|---|
| 33[a] | (propyl-phenyl with CF₃) | " | " | " | 67.8 |

[a]Hydrochloride
[b]Oxalate

TABLE 3

(phenyl-NO₂)—CH=C(COOCH₃)(COOR¹)  +  H₂N—(pyrazole with R³, R²)  →  (I')
(II')    (III)

| Example No. | Amount used g (mmol.) Compd. (II') | Compd. (III) | Solvent (ml) | Reaction Temp. (°C.) | Reaction Time (hrs.) |
|---|---|---|---|---|---|
| 2 | 0.88(3.01) | 0.50(3.05) | t-butanol (5) | 80 | 3 |
| 3 | 0.88(3.01) | 0.54(3.01) | t-butanol (6) | 80 | 3 |
| 4 | 0.88(3.01) | 0.54(3.01) | i-propanol (2) | 70 | 72 |
| 5 | 0.67(2.0) | 0.33(2.0) | i-propanol (2) | 80 | 15 |
| 6 | 0.57(1.64) | 0.27(1.64) | i-propanol (2) | 80 | 24 |
| 7 | 1.04(2.87) | 0.47(2.87) | i-propanol (10) | 80 | 20 |
| 8 | 0.64(2.0) | 0.33(2.0) | i-propanol (2) | 80 | 24 |
| 9 | 0.71(2.0) | 0.33(2.0) | i-propanol (2) | 80 | 24 |
| 10 | 1.00(2.81) | 0.47(2.87) | i-propanol (10) | 80 | 3 |
| 11 | 0.90(2.53) | 0.45(2.53) | i-propanol (9) | 80 | 20 |
| 12 | 0.62(2.0) | 0.33(2.0) | i-propanol (2) | 80 | 24 |
| 13 | 0.64(2.0) | 0.33(2.0) | i-propanol (4) | 80 | 18 |
| 14 | 2.01(5.08) | 0.84(5.09) | i-propanol (5) | 80 | 17 |
| 15 | 1.01(2.46) | 0.41(2.48) | i-propanol (25) | 80 | 19 |
| 16 | 0.89(2.92) | 0.48(2.92) | i-propanol (9) | 80 | 19 |
| 17 | 0.68(2.0) | 0.33(2.0) | i-propanol (2) | 80 | 16 |
| 18 | 0.95(2.54) | 0.42(2.54) | i-propanol (10) | 80 | 20 |
| 19 | 1.13(2.82) | 0.47(2.82) | i-propanol (10) | 80 | 20 |
| 20 | 3.39(9.19) | 1.52(9.19) | t-butanol (10) | 80 | 2 |
| 21 | 4.09(10.9) | 1.81(10.9) | t-butanol (15) | 80 | 3 |
| 22 | 1.0(2.7) | 0.45(2.7) | t-butanol (5) | 80 | 16 |
| 23 | 0.92(2.72) | 0.45(2.7) | i-propanol (5) | 80 | 20 |
| 24 | 1.08(2.96) | 0.49(2.96) | i-propanol (5) | 80 | 20 |
| 25 | 1.05(3.15) | 0.52(3.15) | i-propanol (5) | 80 | 20 |
| 26 | 1.33(4.0) | 0.66(4.0) | t-butanol (10) | 80 | 20 |
| 27 | 1.02(3.34) | 0.55(3.34) | i-propanol (5) | 80 | 20 |
| 28 | 1.01(3.19) | 0.53(3.19) | i-propanol (5) | 80 | 19 |
| 29 | 1.07(2.86) | 0.47(2.86) | i-propanol (8) | 80 | 2.5 |
| 30 | 1.00(2.51) | 0.42(2.51) | i-propanol (6) | 80 | 3 |
| 31 | 2.00(4.9) | 0.81(4.9) | i-propanol (10) | 80 | 24 |
| 32 | 1.67(4.0) | 0.66(4.0) | i-propanol (10) | 70 | 48 |
| 33 | 1.22(3.0) | 0.50(3.0) | i-propanol (10) | 70 | 48 |

TABLE 4

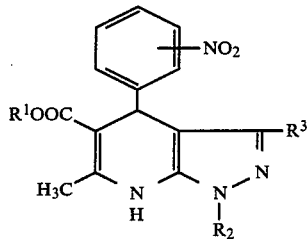

(I')

| Example No. | Appear-[c] ance | Solvent for Recrystallization | m.p. (°C.) | Molecular Formula | Calcd. C | Calcd. H | Calcd. N | Found C | Found H | Found N |
|---|---|---|---|---|---|---|---|---|---|---|
| 2[a] | YP | ethanol | 167–173 | $C_{23}H_{29}ClN_4O_5$ | 57.92 | 6.13 | 11.75 | 57.84 | 6.18 | 11.65 |
| 3 | YP | ethanol | 200–202 | $C_{24}H_{30}N_4O_5$ | 63.42 | 6.65 | 12.33 | 63.26 | 6.41 | 12.36 |
| 4 | YN | i-propyl ether | 148–149 | $C_{24}H_{30}N_4O_5$ | 63.42 | 6.65 | 12.33 | 63.37 | 6.57 | 12.39 |
| 5 | YP | i-propyl ether | 101–103 | $C_{26}H_{34}N_4O_5$ | 64.71 | 7.10 | 11.61 | 64.89 | 7.07 | 11.53 |
| 6[a] | YP | acetone | 119–121[a] | $C_{27}H_{35}ClN_4O_5 \cdot H_2O$ | 59.06 | 6.79 | 10.20 | 59.15 | 6.55 | 10.08 |
| 7[a] | YP | acetone/ether | 115–118[a] | $C_{28}H_{37}ClN_4O_5$ | 61.70 | 6.84 | 10.28 | 61.61 | 6.85 | 10.01 |
| 8 | YP | i-propanol | 153–154 | $C_{25}H_{30}N_4O_5$ | 64.36 | 6.48 | 12.01 | 64.25 | 6.47 | 11.90 |
| 9[b] | YP | methylene chloride | 171–173[b] | $C_{30}H_{32}N_4O_9 \cdot H_2O$ | 59.01 | 5.61 | 9.18 | 58.59 | 5.20 | 8.74 |
| 10[a] | P | acetone | 145–150[a] | $C_{28}H_{31}ClN_4O_5$ | 62.39 | 5.80 | 10.39 | 62.17 | 5.81 | 10.33 |
| 11[a] | YP | acetone | 125–130[a] | $C_{29}H_{33}ClN_4O_5 \cdot H_2O$ | 61.00 | 6.18 | 9.81 | 60.59 | 5.99 | 9.66 |
| 12 | YP | i-propyl ether | 124–126[b] | $C_{25}H_{30}N_4O_8S \cdot \frac{1}{2}H_2O$ | 54.04 | 5.62 | 10.08 | 54.28 | 5.38 | 10.05 |
| 13[b] | YP | acetone | 134–136[b] | $C_{27}H_{35}N_5O_8 \cdot 2H_2O$ | 54.63 | 6.62 | 11.80 | 54.73 | 6.21 | 11.87 |
| 14 | YA | — | — | $C_{33}H_{37}N_5O_8$ | | | | | | |
| 15[b] | YP | methanol | 180–182[b] | $C_{34}H_{39}N_5O_8 \cdot \frac{1}{2}H_2O$ | 62.37 | 6.16 | 10.70 | 62.23 | 6.15 | 10.71 |
| 16[a] | YP | ethyl acetate | 110–113[a] | $C_{24}H_{33}ClN_4O_4$ | 60.44 | 6.97 | 11.75 | 60.01 | 6.97 | 11.45 |
| 17[b] | YN | acetone | 180–182[b] | $C_{30}H_{32}N_4O_8 \cdot H_2O$ | 60.60 | 5.76 | 9.42 | 60.60 | 5.44 | 9.33 |
| 18[a] | YP | acetone | 166–170[a] | $C_{28}H_{30}Cl_2N_4O_4$ | 60.33 | 5.42 | 10.05 | 60.10 | 5.52 | 9.85 |
| 19[a] | YP | acetone | 128–130[a] | $C_{30}H_{35}ClN_4O_6 \cdot \frac{1}{2}H_2O$ | 60.86 | 6.13 | 9.46 | 61.02 | 6.20 | 9.12 |
| 20 | YA | — | | $C_{29}H_{32}N_4O_5$ | 67.42 | 6.24 | 10.85 | | | |
| 21 | Pl | acetone | 164–170[a] | $C_{30}H_{41}ClN_4O_4$ | 64.68 | 7.42 | 10.06 | 64.61 | 7.41 | 9.98 |
| 22[a] | YN | acetone | 125–127[a] | $C_{28}H_{31}ClN_4O_4$ | 60.58 | 5.63 | 10.09 | 60.60 | 5.91 | 9.63 |
| 23[a] | YP | acetone | 152–155[a] | $C_{25}H_{33}ClN_4O_4S$ | 57.63 | 6.38 | 10.75 | 57.43 | 6.43 | 10.63 |
| 24[a] | YP | acetone | 148–150[a] | $C_{27}H_{35}ClN_4O_4S$ | 59.28 | 6.45 | 10.24 | 59.30 | 6.66 | 10.21 |
| 25[a] | YP | acetone | 145–150[a] | $C_{27}H_{35}ClN_4O_4$ | 62.97 | 6.85 | 10.88 | 62.64 | 6.97 | 10.80 |
| 26[a] | YP | ethanol | 179–184[a] | $C_{27}H_{35}ClN_4O_4$ | 62.96 | 6.85 | 10.88 | 62.78 | 6.81 | 10.73 |
| 27[a] | YP | acetone | 141–150[a] | $C_{25}H_{31}ClN_4O_4$ | 61.66 | 6.42 | 11.50 | 61.21 | 6.31 | 11.30 |
| 28[a] | YP | acetone | 150–155[a] | $C_{26}H_{33}ClN_4O_4$ | 62.33 | 6.64 | 11.18 | 62.10 | 6.46 | 11.25 |
| 29[a] | YP | " | 137–140[a] | $C_{28}H_{30}ClN_4O_4$ | 60.32 | 5.42 | 10.05 | 60.20 | 5.65 | 9.68 |
| 30[a] | YP | ethanol | 150–152[a] | $C_{30}H_{35}ClN_4O_6$ | 61.80 | 6.05 | 9.61 | 61.77 | 5.95 | 9.54 |
| 31[a] | YN | " | 124–126[a] | $C_{28}H_{29}ClN_4O_4 \cdot \frac{1}{2}H_2O$ | 56.23 | 5.02 | 9.36 | 56.66 | 5.42 | 8.90 |
| 32[a] | YP | " | 197–200[a] | $C_{28}H_{30}BrClN_4O_4$ | 55.82 | 4.98 | 9.30 | 55.62 | 4.90 | 9.30 |
| 33[a] | CP | " | 147–149[a] | $C_{29}H_{30}ClF_3N_4O_4$ | 58.88 | 5.07 | 9.47 | 58.78 | 4.96 | 9.40 |

[a]Hydrochloride,
[b]Oxalate
[c]YP = Yellow prism; YN = Yellow Needles; YA = Yellow Amorphous; P = Colorless Prisms; Pl = Colorless Plates

TABLE 5

| Example No. | IR ($\nu_{max}^{cm-1}$) NH | CO | $NO_2$ | NMR ($\delta_{ppm}^{CDCl_3}$)* |
|---|---|---|---|---|
| 2 | 3440 | 1690 | 1350 | 1.25–1.92(8H, m), 2.38, 3.32, 3.63(3H × 3, s), 2.58(1H, m), 3.51(2H, m), 4.14(2H, m), 5.25(1H, s), 7.13–8.08(5H, m) |
| 3 | 3270 | 1695 | 1360 | 0.77–2.32(10H, m), 2.35, 3.28, 3.65(3H × 3, s), 2.50(1H, m), 3.50(2H, m), 4.13(2H, m), 5.95(1H, s), 7.00(1H, br.s), 7.13–7.80(4H, m) |
| 4 | 3270 | 1698 | 1378 | 0.83–1.77(9H, m), 2.27–2.48(2H, m), 2.38, 3.30, 3.67(3H × 3, s), 3.45(2H, t), 4.10(2H, t), 5.90(1H, s), 6.25(1H, br.s), 7.07–7.77(4H, m) |
| 5 | 3240 | 1692 | 1355 | 0.95–2.03(10H, m), 1.06(6H, d), 2.37, 3.67(3H × 2, s), 2.89(1H, m), 3.33(3H, m), 4.04(2H, t), 5.90(1H, s), 6.68(1H, br.s), 7.10–7.77(4H, m) |
| 6 | 3430 | 1690 | 1355 | 1.01–2.13(16H, m), 2.36, 3.66(3H × 2, s), 2.58–3.20(1H, m), 3.28–4.33(3H, m), 5.91(1H, s), 6.26(1H, br.s), 7.03–7.77(4H, m) |
| 7 | 2570–2690 | 1685 | 1365[a] | 1.01–3.37(20H, m), 2.33, 3.65(3H × 2, s), 3.50(2H, t), 3.80–4.33(2H, m), 5.92(1H, s), 6.90(1H, br.s), 7.07–7.73(4H, m) |
| 8 | 3250 | 1688 | 1360 | 0.93–2.17(12H, m), 2.33, 3.68(3H × 2, s), 2.67–3.13(1H, m), 3.47–4.27(5H, m), 5.93(1H, s), 7.00–7.83(5H, m) |
| 9 | 2300 | 1730 1700 | 1378[b] | 1.05–1.93(8H, m), 2.33, 3.63(3H × 2, s), 2.63–3.12(1H, m), 3.77–4.47(4H, m), 5.95(1H, s), 6.70–7.78(4H, m) |
| 10 | 2530 | 1700 | 1360[a] | 1.22–2.80(9H, m), 2.42, 3.67(3H × 2, s), 4.07, 4.37(2H × 2, m), 5.27(1H, s), 7.05(1H, br.s), 7.05–8.08(9H, m) |
| 11 | 2530–2650 | 1679 | 1357[a] | 0.83–2.77(11H, m), 2.35, 3.63(3H × 2, s), 3.92–4.08(2H, m), 4.17–4.50(2H, m), 3.91(1H, s), 6.90(1H, br.s), 6.75–7.70(9H, m) |
| 12 | 2300 | 1702 | 1378[b] | 1.00–3.20(11H, m), 2.07, 2.35, 3.65(3H × 3, s), 3.83–4.33(2H, m), 5.90(1H, s), 7.00–8.03(4H, m) |
| 13 | 3430 | 1690 | 1355 | 1.10–2.58(11H, m), 2.22(6H, s), 2.38, 3.70(3H × 2, s), 2.72–3.23(2H, m), 3.57–4.30(2H, m), 5.91(1H, s), 6.95–7.81(4H, m) |

TABLE 5-continued

| Example No. | IR ($\nu_{max}^{cm-1}$) NH | CO | NO$_2$ | NMR ($\delta_{ppm}^{CDCl_3}$)* |
|---|---|---|---|---|
| 14 | 3430 | 1685 | 1350 | 1.08–3.03(15H, m), 2.30, 3.58(3H × 2, s), 3.50(2H, s), 4.87–5.20(1H, m), 6.02(1H, s), 7.01–7.85(10H, m) |
| 15 | 3430 | 1680 | 1350 | 1.12–3.00(17H, m), 2.32, 3.63(3H × 2, s), 3.42(2H, s), 4.43–4.90(1H, m), 6.21 (1H, s), 7.10–7.86(9H, m) |
| 16 | 2570–2675 | 1697 | 1357$^a$ | 0.77–3.16(18H, m), 2.34, 3.63(3H × 2, s), 3.75–4.07(2H, m), 5.92(1H, s), 6.98 (1H, br.s), 7.07–7.73(4H, m) |
| 17 | 2300 | 1733 1700 | 1375$^b$ | 1.10–2.00(8H, m), 2.27, 3.62(3H × 2, s), 2.57–3.27(3H, m), 3.87–4.50(2H, m), 5.93(1H, s), 7.00–8.27(9H, m) |
| 18 | 2370 | 1705 | 1360$^a$ | 1.10–3.20(9H, m), 2.29, 3.67(3H × 2, s), 2.73(2H, t), 3.90–4.37(2H, m), 5.88(1H, s), 6.74(1H, br.s), 6.99–7.73(8H, m) |
| 19 | 2360 | 1699 | 1348$^a$ | 1.11–3.18(9H, m), 3.30, 3.64(3H × 2, s), 2.70(2H, t), 3.82(6H, s), 3.93–4.29(2H, m), 5.90(1H, s), 6.72(3H, s), 6.83(1H, br.s), 7.07–7.73(4H, m) |
| 20 | 3430 | 1690 | 1350 | 1.10–2.77(9H, m), 2.37, 3.20, 3.24, 3.66(3H × 4, s), 3.97–4.50(3H, m), 5.22(1H, s) 6.92(1H, br.s), 7.12–8.08(9H, m) |
| 21 | 3425 | 1675 | 1340 | 0.37–2.70(27H, m), 4.67(1H, m), 2.38, 2.45, 3.66(3H × 3, s), 5.20, 5.27(1H, 2s), 6.80, 6.93(1H, 2 br.s), 7.20–8.12(4H, m) |
| 22 | 2700 | 1694 | 1352$^a$ | 1.0–1.93(8H, m), 2.3(3H, s), 2.67–3.23(3H, m), 3.6(3H, s), 3.83–4.33(2H, m), 5.85(1H, s) 6.87–8.03(9H, m) |
| 23 | 2670 | 1705 | 1363$^a$ | 1.0–3.20(9H, m), 1.23(3H × 2, d), 2.37, 3.67(3H × 2, s), 2.56(2H, t), 2.93(1H, sep), 3.83–4.30(2H, m), 5.90(1H, s), 7.0(1H, br.s), 7.12–7.77(4H, m) |
| 24 | 2480 | 1701 | 1359$^a$ | 1.03–3.30(18H, m), 2.38, 3.68(3H × 2, s), 2.58(2H, t), 3.87–4.33(2H, m), 5.91(1H, s), 6.88(1H, br.s), 7.13–7.77(4H, m) |
| 25 | 2520 | 1700 | 1358$^a$ | 0.77–3.10(20H, m), 2.33, 3.62(3H × 2, s), 3.73–4.17(2H, m), 5.90(1H, s), 6.83 (1H, br.s), 7.07–7.73(4H, m) |
| 26 | 2450 | 1701 | 1355$^a$ | 0.53–2.30(19H, m), 2.38(3H, s), 2.71–3.20(1H, m), 3.50–4.28(2H, m), 3.68(3H, s), 5.94(1H, s), 6.52(1H, br.s), 7.10–7.81(4H, m) |
| 27 | 2530 | 1683 | 1358 | 1.03–3.17(17H, m), 2.32, 3.62(3H × 2, s), 5.03(1H, m), 6.03(1H, s), 6.90(1H, br.s), 7.10–7.82(4H, m) |
| 28 | 2525 | 1702 | 1355$^a$ | 0.9–3.13(19H, m), 2.36, 3.63(3H × 2, s), 4.62(1H, m), 6.03(1H, s), 6.82(1H, br.s), 7.10–7.84(4H, m) |
| 29 | 3420 3270 | 1685 | 1350 | 1.15–2.0(8H, m), 2.35(3H, s), 2.60(1H, m), 2.70–2.93(2H, m), 3.66(3H, s), 4.04–4.37 (2H, m), 5.12(1H, s), 6.35(1H, s), 6.99–8.01(8H, m) |
| 30 | 3420 3280 | 1685 | 1350 | 1.15–1.72(8H, m), 2.36(3H, s), 2.58(1H, m), 2.83(2H, m), 3.67(3H, s), 3.85(6H, s), 4.24(2H, m), 5.20(1H, s), 6.63–8.05(8H, m) |
| 31 | 2670 | 1700 | 1375$^a$ | 1.07–3.32(9H, m), 2.30(3H, s), 2.75(2H, t), 3.67(3H, s), 4.17(2H, t), 5.90(1H, s), 6.83–7.80(4H, m), 8.27(1H, s) |
| 32 | 2380 | 1713 | 1355$^a$ | 1.07–2.0(8H, m), 2.27(3H, s), 2.72(2H, t), 2.72–3.18(1H, m), 3.62(3H, s), 5.87(1H, s), 6.83–7.83(8H, m) |
| 33 | 2680 | 1715 | 1338$^a$ | 1.07–2.13(8H, m), 2.25(3H, s), 2.55–3.20(1H, m), 2.83(2H, t), 3.62(3H, s), 4.17(2H, t), 5.87(1H, s), 6.97–7.83(8H, m) |

$^a$Hydrochloride,
$^b$Oxalate
*Data of NMR are shown as those on free bases.

EXAMPLE 34 (Part 2)

Components for tablet

| | |
|---|---|
| Phenethyl 3-cyclopentyl-1,6-dimethyl-4-(2-nitrophenyl)-4,7-dihydropyrazolo[3,4-b]pyridine-5-carboxylate | 10 mg |
| Corn starch | 50 mg |
| Gelatin | 7.5 mg |
| Avicel | 25 mg |
| Magnesium stearate | 2.5 mg |
| Total | 95 mg |

These substances are formulated into a tablet.

PREPARATION 1 (Part 2)

Preparation of 2-methoxyethyl 2-nitrobenzylideneacetoacetate 6

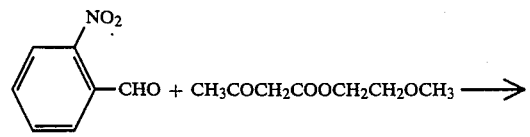

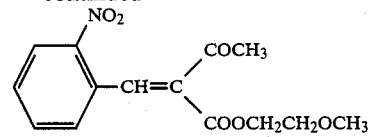

A solution of 4.80 g (30.0 mMol) of methoxyethylacetoacetate 5, 4.53 g (30.0 mMol) of 2-nitrobenzaldehyde 4, 1.0 ml of acetic acid and 0.3 ml of piperidine in 25 ml of benzene is stirred at room temperature for 17 hours, and the mixture is refluxed for 2 hours in a condition of azeotropic distillation. The reaction mixture is washed with water, dried over magnesium sulfate, filtered, and evaporated. The residue is chromatographed on silica gel for purification to give 7.93 g (90.2% yield) of the titled compound 6 as an yellow oil [from the eluate with dichloromethane/ethyl acetate (95/5)]. NMR(CDCl$_3$) δ ppm: 2.23, 2.48(3H, 2s), 3.17–3.80(2H, m), 3.22, 3.40(3H, 2s), 4.08–4.53(2H, m), 7.33–8.33(5H, m).

PREPARATIONs 2-30 (Part 2)

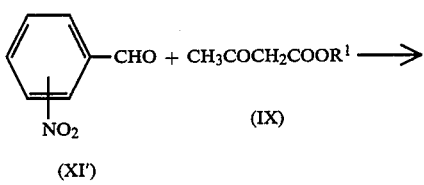

(XI')

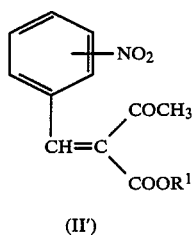

(II')

wherein $R^1$ has the same meaning as defined above.

A solution of the compound (XI') and a compound (IX) in a solvent is allowed to react in the presence of an organic base at room temperature or under heating, and then refluxed if needed. The reaction mixture is washed with water, dried, filtered, and evaporated. According to the requisition, the resulting residue is subjected to recrystallization or chromatography on silica gel in order to purify.

Each of the compounds (II') listed in the following Table 6 can be prepared in the above-depicted manner. The yield for a compound (II') is listed in Table 6 (Part 2). The process for production of the starting substances (IX) is depicted over the top of Table 6 (Part 2), the yield of which is also listed in Table 6 (Part 2). In addition, the detailes of the reaction conditions for the above reaction (Preparations 2-25 as Part 2) are summarized in Table 7 (Part 2). Data of melting point and NMR spectrum on each of the compounds (II') and the starting substances (IX) are summarized in Table 5 (Part 2).

TABLE 6

$$CH_2 \overset{O}{\underset{O}{\diagdown}} + R^1OH \longrightarrow$$

(XIII)    (XIV)

$$CH_3COCH_2COOR^1 \longrightarrow$$

(IX)

| Prepn. No. | R' | Yield of (IX) (%) | Position of —NO₂ | Yield of (II') (%) |
|---|---|---|---|---|
| 2 | —CH₂CH₂OCH₃ | Compd. marketed | 3 | 88.4 |
| 3 | —CH₂CH₂CH₂OCH(CH₃)₂ | 72.7 | 2 | 50.7 |
| 4 | —CH₂CH₂O-(cyclopentyl) | 68.1 | " | 84.0 |
| 5 | —CH₂CH₂O-(cyclohexyl) | 94.1 | " | 91.6 |
| 6 | —CH₂-(oxetane) | 74.6 | " | 79.4 |
| 7 | —CH₂CH₂.O-(phenyl) | 86.5 | " | 94.4 |
| 8 | " | " | 3 | 75.9 |
| 9 | —CH₂CH₂SCH₃ | 25.1 | 2 | 86.7 |

TABLE 6-continued
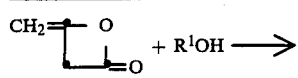
(XIII)   (XIV)
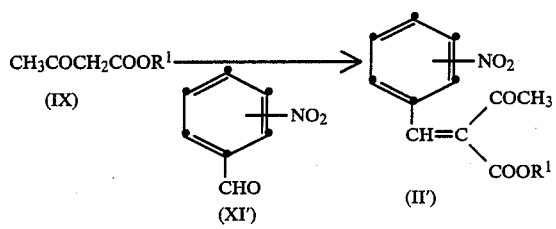
| Prepn. No. | R' | Yield of (IX) (%) | Position of —NO$_2$ | Yield of (II') (%) |
|---|---|---|---|---|
| 10 | —CH$_2$CH$_2$CH$_2$N(CH$_3$)$_2$ | 79.0 | " | 53.1 |
| 11** | pyrrolidinyl-N—CH$_2$—C$_6$H$_5$ | 95.0 | " | 84.6 |
| 12 | piperidinyl-N—CH$_2$—C$_6$H$_5$ | 81.0 | " | 62.2 |
| 13 | —(CH$_2$)$_4$CH$_3$ | 77.0 | " | 89.0 |
| 14 | —CH$_2$CH$_2$—C$_6$H$_5$ | 89.3 | " | 88.2 |
| 15 | —CH$_2$CH$_2$—C$_6$H$_4$—Cl | 95.8 | " | 96.0 |
| 16 | —CH$_2$CH$_2$—C$_6$H$_3$(OCH$_3$)$_2$ | 92.9 | 2 | 96.8 |
| 17 | —CH(OCH$_3$)CH$_2$—C$_6$H$_5$ | 89.6 | 3 | 87.5 |
| 18* | 2,5-dimethyl-4-isopropylphenyl | 89.4 | 3 | 71.2 |

TABLE 6-continued
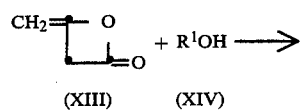
(XIII)   (XIV)
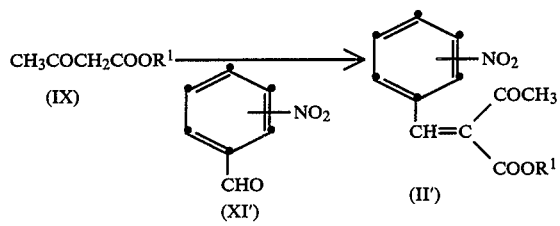
| Prepn. No. | R' | Yield of (IX) (%) | Position of —NO$_2$ | Yield of (II') (%) |
|---|---|---|---|---|
| 19 | —CH$_2$CH$_2$S—C$_6$H$_5$ | 99.6 | 2 | 84.2 |
| 20 | —CH$_2$CH$_2$S—CH(CH$_3$)$_2$ | 96.6 | " | 93.2 |
| 21 | —CH$_2$CH$_2$—S—(cyclopentyl) | 92.1 | " | 92.4 |
| 22 | —CH$_2$CH$_2$—(cyclopentyl) | 96.6 | " | 97.4 |
| 23 | —CH$_2$—(cyclohexyl) | 94.5 | " | 85.5 |
| 24 | (cyclopentyl) | 92.9 | " | 97.7 |
| 25 | (cyclohexyl) | 93.5 | " | 97.3 |
| 26 | —CH$_2$CH$_2$—C$_6$H$_4$—Cl | vide supra | 3 | 98.0 |
| 27 | —CH$_2$CH$_2$—C$_6$H$_3$(OMe)$_2$ | vide supra | 3 | 90.4 |

TABLE 6-continued

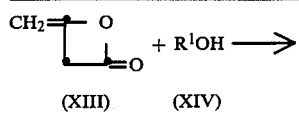

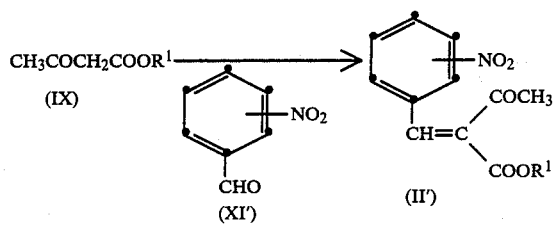

| Prepn. No. | R' | Yield of (IX) (%) | Position of —NO₂ | Yield of (II') (%) |
|---|---|---|---|---|
| 28 | (3,4-dichlorophenethyl) | 90.6 | 2 | 93.1 |
| 29 | (4-bromophenethyl) | 98.1 | 2 | 76.5 |
| 30 | (3-trifluoromethylphenethyl) | 97.2 | 2 | 54.1 |

*(IX)-18: Disclosed in F. Korte, F. Wuesten, Liebigs Ann., 647, 18 (1961)
**Material for (IX)-11,

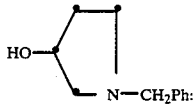

Disclosed in E. Jaeger, J. H. Biel, J. Org. Chem, 30, 740 (1965)
Ph = Phenyl

TABLE 7

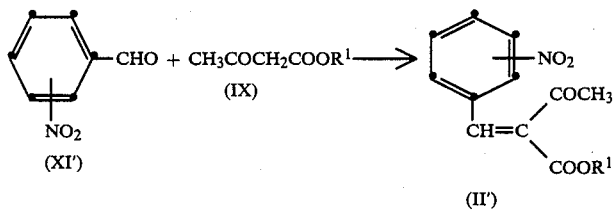

| Prepn. No. | Amount used g (mmol.) Compd.(XI') | Compd.(IX) | Solvent (ml) | Reaction Temp. (°C.) | Reaction Time (hrs.) |
|---|---|---|---|---|---|
| 2 | 4.53(30.0) | 4.80(30.0) | benzene (25) P(0.1), AcOH(0.3) | r.t. | 21 |
| 3 | 2.04(13.5) | 2.72(13.4) | benzene (5) P(0.1), AcOH(0.2) | r.t. reflux | 100 1 |
| 4 | 0.30(1.96) | 0.42(1.96) | benzene (2) P(0.004), AcOH(0.01) | r.t. reflux | 72 2 |
| 5 | 1.51(10.0) | 2.28(10.0) | benzene (5) P(0.05), AcOH(0.2) | r.t. reflux | 72 3 |
| 6 | 4.53(30.0) | 5.58(30.0) | benzene (10) P(0.1), AcOH(0.4) | r.t. | 72 |
| 7 | 4.76(31.5) | 7.0(31.5) | benzene (10) P(0.05), AcOH(0.2) | 40 reflux | 100 2 |
| 8 | " | " | " | " | " |
| 9 | 3.78(25.0) | 4.4(25.0) | benzene (5) P(0.1), AcOH(0.4) | r.t. | 72 |
| 10 | 4.53(30.0) | 5.62(30.0) | benzene (10) | r.t. | 72 |

TABLE 7-continued

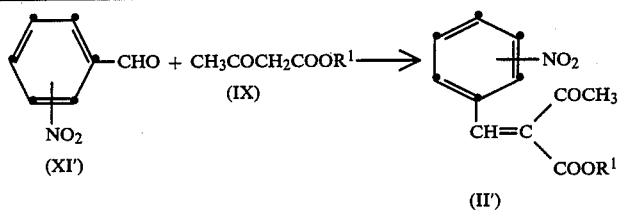

(II')

| Prepn. No. | Amount used g (mmol.) Compd.(XI') | Amount used g (mmol.) Compd.(IX) | Solvent (ml) | Reaction Temp. (°C.) | Reaction Time (hrs.) |
|---|---|---|---|---|---|
| 11 | 0.91(6.01) | 1.57(6.01) | benzene (3) P(0.01), AcOH(0.04) | r.t. reflux | 48 1 |
| 12 | 1.14(7.57) | 2.08(7.57) | benzene (4) P(0.01), AcOH(0.04) | reflux | 4 |
| 13 | 6.14(40.6) | 7.00(40.6) | benzene (10) P(0.05), AcOH(0.2) | 40 reflux | 100 2 |
| 14 | 4.53(30.0) | 6.18(30.0) | benzene (10) P(0.1), AcOH(0.4) | r.t. reflux | 72 3 |
| 15 | 1.51(10.0) | 2.41(10.0) | benzene (5) P(0.05), AcOH(0.2) | r.t. reflux | 72 2 |
| 16 | 1.51(10.0) | 2.66(10.0) | benzene (5) P(0.05), AcOH(0.2) | r.t. reflux | 72 3 |
| 17 | 1.62(10.7) | 2.53(10.7) | benzene (2) P(0.02), AcOH(0.1) | r.t. reflux | 72 7 |
| 18 | 4.0(26.5) | 6.38(26.5) | benzne (10) P(0.05), AcOH(0.2) | r.t. reflux | 72 7 |
| 19 | 3.0(20.0) | 4.76(20.0) | benzne (20) P(0.1), AcOH(0.2) | r.t. reflux | 16 2 |
| 20 | 4.89(32.3) | 6.6(32.3) | benzene (20) P(0.15), AcOH(0.3) | r.t. reflux | 16 1 |
| 21 | 4.34(29.1) | 6.7(29.1) | benzene (20) P(0.15), AcOH(0.3) | r.t. reflux | 16 1 |
| 22 | 3.58(23.7) | 4.7(23.7) | benzene (20) P(0.3), AcOH(0.6) | r.t. reflux | 16 1 |
| 23 | 4.53(30.0) | 5.95(30.0) | benzene (10) P(0.3), AcOH(0.6) | r.t. reflux | 16 1 |
| 24 | 2.66(17.6) | 3.0(17.6) | benzene (6) P(0.05), AcOH(0.2) | r.t. reflux | 16 2 |
| 25 | 2.46(16.3) | 3.0(16.3) | benzene (6) P(0.05), AcOH(0.2) | r.t. reflux | 16 2 |
| 26 | 2.78(18.38) | 4.42(18.37) | benzene (9) P(0.036), AcOH(0.1) | r.t. reflux | 96 2 |
| 27 | 1.0(6.64) | 1.77(6.64) | benzene (4) P(0.013), AcOH(0.038) | r.t. reflux | 96 2 |
| 28 | 1.51(10.0) | 2.75(10.0) | benzene (10) P(0.1), AcOH(1.0) | r.t. reflux | 20 2 |
| 29 | 1.51(10.0) | 2.85(10.0) | benzene (10) P(0.1), AcOH(1.0) | r.t. reflux | 20 2 |
| 30 | 1.51(10.0) | 2.74(10.0) | benzene (10) P(0.1), AcOH(1.0) | r.t. reflux | 20 2 |

*P: Piperidine, AcOH: Acetic acid, r.t.: room temperature

TABLE 8

| Prepn. No. | Boiling Point °C. (mmHg) | NMR ($\delta_{ppm}^{COCl_3}$) |
|---|---|---|
| | | $CH_3COCH_2COOR^1$ (IX) |
| (IX)-3 | 90–91 (0.6) | 1.12(6H,d), 1.93(2H,m), 2.55(3H,s), 3.33–4.02(3H,m), 3.45(2H,s), 4.23(2H,t) |
| 4 | 96–100 (0.1) | 1.15–1.90(8H,m), 2.27(3H,s), 3.36–4.47(5H,m), 3.47(2H,s) |
| 5 | 118–120 (0.4) | 1.15–2.07(10H,m), 2.26(3H,s), 3.25(1H,m), 3.45(2H,s), 3.63, 4.26(2H × 2,t) |
| 6 | 95–100 (0.9) | 1.33–2.17(4H,m), 2.27(3H,s), 3.50(2H,s), 3.53–4.33(4H,m) |
| 7,8 | 140–143 (0.7) | 2.20(3H,s), 3.43(2H,s), 4.03–4.60(4H,m), 6.73–7.43(5H,m) |
| 9 | 160–162 (25) | 2.13, 2.27(3H × 2,s), 2.72(2H,t), 3.45(2H,s), 4.28(2H,t) |
| 10 | 138–141 (23) | 1.40–2.98(4H,m), 2.20(6H,s), 2.23(3H,s), 3.45(2H,s), 4.18(2H,t) |
| 11 | oil | 1.63–2.98(6H,m), 2.23(3H,s), 3.42, 3.63(2H × 2,s), 5.24(1H,m), 7.31(5H,s) |
| 12 | oil | 1.48–2.82(8H,m), 2.23(3H,s), 3.40, 3.47(2H × 2,s), 4.83(1H,m), 7.27(5H,s) |
| (IX)-13 | 106–111 (8) | 0.67–2.17(9H,m), 2.27(3H,s), 3.45(2H,s), 4.13(2H,t) |
| 14 | 100–115 (0.8) | 2.15(3H,s), 2.93(2H,t), 3.38(2H,s), 4.33(2H,t), 7.23(5H,s) |
| 15 | 155–158 (0.7) | 2.18(3H,s), 2.90(2H,t), 3.39(2H,s), 4.30(2H,t), 7.10, 7.26(2H × 2,d) |
| 16 | 182–185 (0.8) | 2.19, 3.82, 3.85(3H × 3,s), 2.88(2H,t), 3.40(2H,s), 4.42(2H,t), 6.75(3H,m) |
| 17 | oil | 2.23, 3.28(3H × 2,s), 3.46(2H,s), 4.37(3H,m), 7.28(5H,s) |
| 18 | 95–101 (0.3) | 0.62–2.35(18H,m), 4.73(1H,m), 2.35(3H,s), 3.42(2H,s) |
| 19 | oil | 2.18(3H,s), 3.08(2H,t), 3.33(3H,s), 4.20(2H,t), 6.97–7.37(5H,m) |
| 20 | oil | 1.25(3H × 2,d), 2.27(3H,s), 2.75(2H,t), 3.02(1H,q), 3.43(2H,s), 4.23(2H,t) |
| 21 | oil | 1.13–2.23(8H,m), 2.47(3H,s), 2.73(2H,t), 2.93–3.27(1H,m), 3.43(2H,s), 4.23(2H,t) |
| 22 | oil | 1.03–2.0(11H,m), 2.23(3H,s), 3.4(2H,s), 4.3(2H,t) |
| (IX)-23 | oil | 0.67–2.03(11H,m), 2.2(3H,s), 3.40(2H,s), 3.95(2H,d) |

TABLE 8-continued

| Prepn. No. | Boiling Point °C. (mmHg) | NMR ($\delta_{ppm}^{CDCl_3}$) |
|---|---|---|
| 24 | 103–106 (6) | 0.96–2.10(8H,m), 2.28(3H,s), 3.43(2H,s), 5.25(1H,m) |
| 25 | 116–119 (6) | 0.97–2.04(10H,m), 2.25(3H,s), 3.42(2H,s), 4.82(1H,m) |
| (IX)-26 | vide supra | vide supra |
| 27 | vide supra | vide supra |
| 28 | oil | 2.18(3H,s), 2.90(2H,t), 3.40(2H,s), 4.30(2H,t), 6.90–7.43(3H,m) |
| 29 | oil | 2.18(3H,s), 2.88(2H,t), 3.40(2H,s), 4.32(2H,t), 6.93–7.53(4H,m) |
| 30 | oil | 2.20(3H,s), 3.02(2H,t), 3.42(2H,s), 4.37(2H,t), 7.43(4H,s) |

(II')

$$\text{Ar-CH}=C\begin{array}{c}COCH_3\\COOR^1\end{array}$$ (with NO$_2$-phenyl)

| (II')-2 | mp. 43–45° C. | 2.43, 3.28(3H × 2,s), 3.50–3.75(2H,m), 4.30–4.55(2H,m), 7.33–8.33(5H,m) |
|---|---|---|
| 3 | oil | 1.08(6H,d), 1.52–2.07(2H,m), 2.47(3H,s), 3.12–4.48(5H,m), 7.27–8.25(5H,m) |
| 4 | oil | 1.07–1.84(8H,m), 2.23, 2.49(3H,2s), 3.17–4.47(5H,m), 7.36–8.31(5H,m) |
| 5 | oil | 0.77–2.10(10H,m), 2.22, 2.47(3H,2s), 3.17(1H,m), 3.43, 3.72(2H,2t), 4.17, 4.42 (2H,2t), 7.27–8.30(5H,m) |
| 6 | oil | 1.03–2.17(4H,m), 2.23, 2.47(3H,2s), 3.47–4.37(5H,m), 7.23–8.36(5H,m) |
| 7 | oil | 2.18, 2.42(3H,2s), 3.70–4.70(4H,m), 6.60–8.23(10H,m) |
| 8 | mp.127–131° C. | 2.44(3H,s), 4.18, 4.65(2H × 2,t), 6.72–8.33(10H,m) |
| (II')-9 | oil | 2.00, 2.17(3H,2s), 2.22, 2.48(3H,2s), 2.45, 2.83(2H,2t), 4.17, 4.45(2H,2t), 7.20–8.33(5H,m) |
| 10 | oil | 1.38–2.33(4H,m), 2.13(6H,s), 2.47(3H,s), 4.05, 4.33(2H,2t), 7.25–8.33(5H,m) |
| 11 | oil | 1.36–3.06(6H,m), 2.20, 2.45(3H,2s), 3.50, 3.65(2H,2s), 4.99–5.48(1H,m), 7.16–8.27(10H,m) |
| 12 | oil | 1.09–2.85(8H,m), 2.18, 2.46(3H,2s), 3.39, 3.51(2H,2s), 4.62–5.25(1H,m), 7.07–8.41(10H,m) |
| 13 | oil | 0.63–2.02(9H,m), 2.20, 2.47(3H,2s), 3.98, 4.27(2H,2t), 7.35–8.27(5H,m) |
| 14 | oil | 2.12, 2.40(3H,2s), 2.68, 3.00(2H,2t), 4.22, 4.47(2H,2t), 6.83–8.23(10H,m) |
| 15 | oil | 2.10, 2.43(3H,2s), 2.68, 3.00(2H,2t), 4.20, 4.48(2H,2t), 6.87–8.30(9H,m) |
| 16 | oil | 2.08, 2.40(3H,2s), 2.62, 2.93(2H,2t), 3.78, 3.83, 3.85(6H,3s), 4.18, 4.45(2H,2t) 6.43–8.30(8H,m) |
| (II')-17 | oil | 2.33, 2.41(3H,2s), 3.20, 3.31(3H,2s), 4.43(3H,m), 7.28–8.27(10H,m) |
| 18 | oil | 0.48–2.48(18H,m), 4.90(1H,m), 2.38(3H,s), 7.38–8.35(5H,m) |
| 19 | oil | 2.17, 2.42(3H,s), 2.82, 3.18(2H,t), 4.12, 4.37(2H,t), 7.0–8.23(10H,m) |
| 20 | oil | 1.2, 1.32(3H × 2,d), 2.23, 2.5(3H,s), 2.5, 2.87(2H,t), 2.77–3.17(1H,m), 4.15, 4.42(2H,t), 7.23–8.33(5H,m) |
| 21 | oil | 1.07–2.11(8H,m), 2.23, 2.48(3H,s), 2.52, 2.87(2H,t), 2.73–3.33(1H,m), 4.17 4.4(2H,t), 7.27–8.37(5H,m) |
| 22 | oil | 0.67–2.0(11H,m), 2.2, 2.45(3H,s), 3.98, 4.27(2H,t), 7.23–8.3(5H,m) |
| 23 | oil | 0.5–2.0(11H,m), 2.2, 2.43(3H,s), 3.8, 4.07(2H,d), 7.27–8.33(5H,m) |
| 24 | oil | 1.17–2.07(8H,m), 2.20, 2.47(3H,s), 5.0–5.50(1H,m), 7.30–8.29(4H,m) |
| 25 | oil | 0.83–2.17(10H,m), 2.22, 2.47(3H,s), 4.57–5.17(1H,m), 7.30–8.28(5H,m) |
| (II')-26 | oil | 2.25, 2.37(3H,s), 2.80–3.09(2H,m), 4.35–4.57(2H,m), 6.91–8.29(9H,m) |
| 27 | oil | 2.27, 2.38(3H,s), 2.78–3.04(2H,m), 3.77, 3.80(3H,s), 3.83, 3.87(3H), 4.35–4.57(2H,m) 6.59–8.28(8H,m) |
| 28 | oil | 2.12, 2.43(3H,s), 2.67, 2.97(2H,t), 4.20, 4.45(2H,t), 6.72–8.27(7H,m) |
| 29 | oil | 2.12, 2.40(3H,s), 2.63, 2.95(2H,t), 4.18, 4.43(2H,t), 6.73–8.27(9H,m) |
| 30 | oil | 2.10, 2.40(3H,s), 2.77, 3.08(2H,t), 4.23, 4.48(2H,t), 7.10–8.27(9H,m) |

PREPARATION 31 (Part 2)

(i) Preparation of 3-cyclopentylcarbonylacetonitrile 9

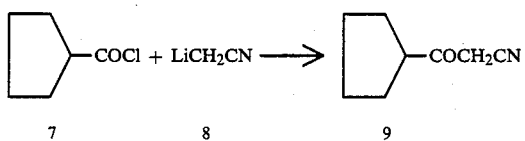

To 20 ml of tetrahydrofuran is added 15.6 ml (26 mMol) of butyl lithium in an atmosphere at −78° C., and 1.3 g (32 mMol) of acetonitrile is dropwisely added to the mixture over the period of 40 minutes. Two hours later, 3.43 g (25.9 mMol) of cyclopentylcarbonyl chloride 7 is further added dropwisely over a period of 40 minutes. The reaction mixture is, after being stirred for 2 hours, neutralized with 10% hydrochloric acid and extracted with ether. The extract solution is dried over magnesium sulfate, filtered, and then evaporated. The resulting residue is subjected to column chromatography to give 2.91 g (80.8% yield) of the titled compound 9 as an oil (from the chloroform layer).

NMR(CDCl$_3$) δ ppm: 1.43–2.2 (8H, m), 2.7–3.33 (1H, m), 3.53 (2H, s).

(ii) Preparation of 5-amino-3-cyclopentyl-1-methylpyrazole 11

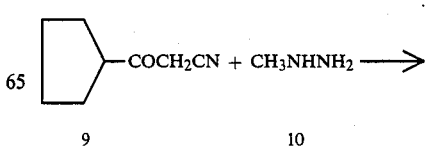

-continued

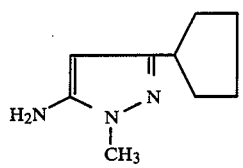

11

To a solution of 13.21 g (96.3 mMol) of 3-cyclopentylcarbonylacetonitrile 9 in 10 ml of dioxane is added 4.44 g (96.3 mMol) of methylhydrazine 10 under ice-cooling, and the mixture is stirred at room temperature for 17 hours. The reaction mixture is evaporated. The resulting residue is recrystallized from ethyl acetate/hexane (5/2) to give 12.9 g (80.8% yield) of the titled compound 11 as colorless needles, mp. 149°–150° C.

NMR(CDCl$_3$) δ ppm: 1.33–2.20 (8H, m), 2.60–3.10 (1H, m), 3.57 (5H, s), 5.32 (1H, s).

PREPARATIONS 32 and 33 (Part 2)

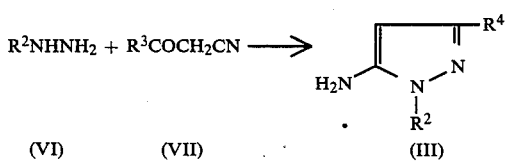

wherein R$^2$ and R$^3$ have the same meanings as defined above respectively.

A solution of compounds (VI) and (VII) in a solvent is allowed to react at room temperature, then evaporated, and the resulting residue is purified by recrystallization, if needed.

In the above-depicted manner, the compounds (III) can be prepared. Details of the reaction conditions are summarized in Table 9 (Part 2), and data such as yield, melting points, and NMR spectrum on the compounds are in Table 10 (Part 2).

TABLE 9

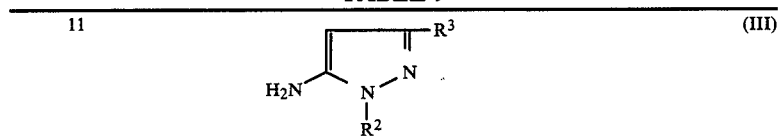

| Prepn. No. | R$^2$ | R$^3$ | Amount used g(mmol.) Compd. (VI) | Amount used g(mmol.) Compd.(VII) | Solvent (ml) | Reaction Time (hrs.) |
|---|---|---|---|---|---|---|
| 32 | CH$_3$ | cyclohexyl | 1.90(41.3) | 6.05(40.0) | ethanol (10) | 24 |
| 33 | CH$_3$ | —CH$_2$—cyclopentyl | 1.43(31.0) | 4.60(30.4) | ethanol (8) | 15 |

TABLE 10

| Prepn. No. | R$^2$ | R$^3$ | Yield (%) | Melting Point (°C.) | NMR: $\delta_{ppm}^{CDCl_3}$ |
|---|---|---|---|---|---|
| 32 | —CH$_3$ | cyclohexyl | 71.7 | 172~174 | 0.90~2.77(11H, m), 3.43(2H, br, s), 3.57(3H, s), 5.32(1H, s) |
| 33 | —CH$_3$ | —CH$_2$—cyclopentyl | 64.9 | 106~107 | 0.93~2.32(9H, m), 2.47(2H, m), 3.51(3H, s), 3.60(2H, br, s), 5.28(1H, s) |

What is claimed is:

1. A 4,7-dihydropyrazolo[3,4-b]-pyridine derivative represented by the formula:

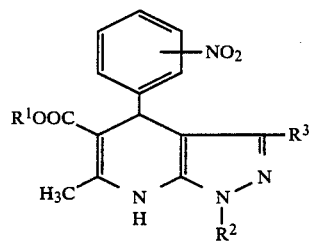

wherein R$^1$ is (a) straight or branched chain C$_5$–C$_8$ alkyl, (b) C$_4$–C$_6$ cycloalkyl which may be substituted by lower alkyl, (c) C$_3$–C$_7$ cycloalkyl (C$_1$–C$_4$)alkyl, (d) C$_1$–C$_4$ alkoxy-(C$_1$–C$_4$)alkyl, (e) C$_4$–C$_7$ cycloalkyloxy(C$_1$–C$_4$)alkyl, (f) phenoxy(C$_1$–C$_4$)alkyl, (g) C$_1$–C$_4$ alkylthio(C$_1$–C$_4$)alkyl, (h) C$_4$–C$_7$ cycloalkylthio(C$_1$–C$_4$)alkyl, (i) phenylthio(C$_1$–C$_4$)alkyl, (j) C$_1$–C$_4$ monalkylamino or C$_2$–C$_8$ dialkylamino-substituted (C$_1$–C$_4$)alkyl, (k) tetrahydrofuryl(C$_1$–C$_4$)alkyl, (l) phenyl(C$_1$–C$_3$)alkyl, which may have one or more substituents of halogen or $C_1$–$C_4$ alkoxy, (m) N-benzylpyrrolidinyl, or (n) N-benzylpiperidinyl; $R^2$ is $C_1$–$C_4$ alkyl; and $R^3$ is $C_4$–$C_6$ cycloalkyl or $C_3$–$C_7$ cycloalkyl($C_1$–$C_4$)alkyl; and the pharmaceutically acceptable acid addition salts thereof.

2. A compound as claimed in claim 1 in which R' is a halogenphenyl ($C_1$–$C_3$) alkyl.

3. A compound claimed in claim 1, namely, cyclopentyloxyethyl 3-cyclopentyl-1,6-dimethyl-4-(2-nitrophenyl)-4,7-dihydropyrazolo-[3,4-b]pyridine-5-carboxylate.

4. A compound claimed in claim 1, namely, methylthioethyl 3-cyclopentyl-1,6-dimethyl-4-(2-nitrophenyl)-4,7-dihydropyrazolo[3,4-b]pyridine-5-carboxylate.

5. A compound claimed in claim 1, namely, phenethyl 3-cyclopentyl-1,6-dimethyl-4-(2-nitrophenyl)-4,7-dihydropyrazolo[3,4-b]-pyridine-5-carboxylate.

6. A compound claimed in claim 1, namely, cyclopentylethyl 3-cyclopentyl-1,6-dimethyl-4-(2-nitrophenyl)-4,7-dihydropyrazolo[3,4-b]pyridine-5-carboxylate.

7. A compound claimed in claim 1, namely, (3-thienyl)ethyl 3-cyclopentyl-1,6-dimethyl-4-(2-nitrophenyl)-4,7-dihydropyrazolo[3,4-b]pyridine-5-carboxylate.

8. A 4,7-dihydropyrazolo[3,4-b]pyridine derivative represented by the formula:

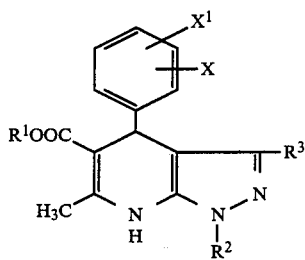

wherein X and $X^1$ each is hydrogen, nitro, or halogen which may be located at the position or positions 2, 3, and/or 6;

$R^1$ is $C_1$–$C_4$ alkyl; $R^2$ is hydrogen, $C_1$–$C_4$ alkyl, $C_4$–$C_6$ cycloalkyl, or phenyl;

$R^3$ is hydrogen, $C_1$–$C_8$ straight or branched chain alkyl, $C_3$–$C_7$ cycloalkyl which may be substituted by $C_1$–$C_3$ alkyl, phenyl which may be substituted by chlorine, trifluoromethyl, cyano, methoxy, methoxycarbonyl or ethoxycarbonyl, $C_7$–$C_9$ aralkyl or $C_1$–$C_4$ alkoxycarbonyl; or pharmaceutically acceptable acid addition salts thereof.

9. A compound claimed in claim 8 wherein X is nitro, X' is hydrogen, $R^1$ is $C_1$–$C_4$ alkyl, $R^2$ is $C_1$–$C_4$ alkyl, $R^3$ is $C_1$–$C_8$ straight or branched chain alkyl, or $C_3$–$C_7$ cycloalkyl.

10. A compound claimed in claim 9 wherein X is located at the 2 or 3 position of the phenyl.

11. A compound claimed in claim 9 wherein $R^3$ is cyclopentyl or cyclohexyl.

12. A compound claimed in claim 8, namely, methyl 3-(n-butyl)-1,6-dimethyl-4-(3-nitrophenyl)-4,7-dihydropyrazolo[3,4-b]pyridine-5-carboxylate.

13. A compound claimed in claim 8, namely, methyl 3-cyclobutyl-1,6-dimethyl-4-(3-nitrophenyl)-4,7-dihydropyrazolo[3,4-b]pyridine-5-carboxylate.

14. A compound claimed in claim 8, namely, methyl 3-cyclopentyl-1,6-dimethyl-4-(3-nitrophenyl)-4,7-dihydropyrazolo[3,4-b]pyridine-5-carboxylate.

15. A compound claimed in claim 8, namely, ethyl 3-cyclopentyl-1,6-dimethyl-4-(3-nitrophenyl)-4,7-dihydropyrazolo[3,4-b]pyridine-5-carboxylate.

16. A compound claimed in claim 8, namely, methyl 3-cyclohexyl-1,6-dimethyl-4-(2-nitrophenyl)-4,7-dihydropyrazolo[3,4-b]pyridine-5-carboxylate.

17. An agent for treating cardiovascular diseases, comprising an effective amount for treating cardiovascular diseases of at least one substance selected from 4,7-dihydropyrazolo[3,4-b]pyridine derivatives represented by the formula:

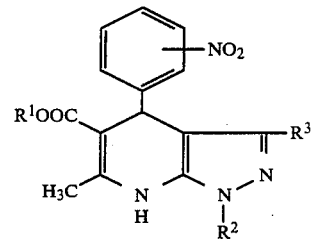

wherein $R^1$ is (a) straight or branched chain $C_5$–$C_8$ alkyl, (b) $C_4$–$C_6$ cycloalkyl which may be substituted by lower alkyl, (c) $C_3$–$C_7$ cycloalkyl ($C_1$–$C_4$)alkyl, (d) $C_1$–$C_4$ alkoxy-($C_1$–$C_4$)alkyl, (e) $C_4$–$C_7$ cycloalkyloxy($C_1$–$C_4$)alkyl, (f) phenoxy($C_1$–$C_4$)alkyl, (g) $C_1$–$C_4$ alkylthio($C_1$–$C_4$)alkyl, (h) $C_4$–$C_7$ cycloalkylthio($C_1$–$C_4$)alkyl, (i) phenylthio($C_1$–$C_4$)-alkyl, (j) $C_1$–$C_4$ monalkylamino or $C_2$–$C_8$ dialkylamino-substituted ($C_1$–$C_4$)alkyl, (k) tetrahydrofuryl($C_1$–$C_4$)alkyl, (l) phenyl($C_1$–$C_3$)alkyl, which may have one or more substituents of halogen or $C_1$–$C_4$ alkoxy, [or trifluoroalkyl,] (m) N-benzylpyrrolidinyl, or (n) N-benzylpiperidinyl; $R^2$ is $C_1$–$C_4$ alkyl; and $R^3$ is $C_4$–$C_6$ cycloalkyl or $C_3$–$C_7$ cycloalkyl($C_1$–$C_4$)alkyl or the pharmaceutically acceptable acid addition salts thereof and a pharmaceutically acceptable carrier.

18. An agent for treating cardiovascular diseases, comprising an effective amount for treating cardiovascular diseases of at least one substance selected from 4,7-dihydropyrazolo[3,4-b]pyridine derivatives represented by the formula:

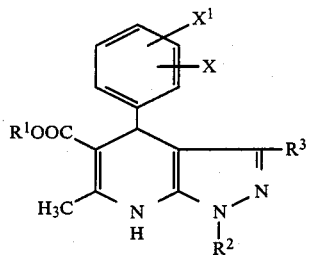

wherein X and $X^1$ each is hydrogen, nitro, or halogen which may be located at the position or positions 2, 3, and/or 6; $R^1$ is $C_1$–$C_4$ alkyl; $R^2$ is hydrogen, $C_1$–$C_4$ alkyl, $C_4$–$C_6$ cycloalkyl, or phenyl; $R^3$ is hydrogen, $C_1$–$C_8$ straight or branched chain alkyl, $C_3$–$C_7$ cycloalkyl which may be substituted by $C_1$–$C_3$ alkyl, phenyl which may be substituted by chlorine, trifluoromethyl, cyano, methoxy, methoxycarbonyl or ethoxycarbonyl, $C_7$–$C_9$ aralkyl or $C_1$–$C_4$ alkoxycarbonyl; or pharmaceutically acceptable acid addition salts thereof and a pharmaceutically acceptable carrier.

* * * * *